United States Patent
Disilvestro et al.

(10) Patent No.: US 7,195,645 B2
(45) Date of Patent: Mar. 27, 2007

(54) IN VIVO JOINT SPACE MEASUREMENT DEVICE AND METHOD

(75) Inventors: Mark R. Disilvestro, Ft. Wayne, IN (US); Jason T. Sherman, Warshaw, IN (US); Terry L. Dietz, Columbia City, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/888,243

(22) Filed: Jul. 9, 2004

(65) Prior Publication Data

US 2005/0010301 A1    Jan. 13, 2005

Related U.S. Application Data

(60) Provisional application No. 60/486,615, filed on Jul. 11, 2003.

(51) Int. Cl.
*A61F 2/30* (2006.01)
*A61B 5/103* (2006.01)

(52) U.S. Cl. .............................. 623/18.11; 623/18.12; 600/587

(58) Field of Classification Search ............ 623/18.11, 623/18.12, 16.11, 22.24, 22.13, 23.16, 23.49, 623/19.11; 600/12, 589, 587; 340/572.8; 235/487

See application file for complete search history.

(56) References Cited

U.S. PATENT DOCUMENTS

| | | | |
|---|---|---|---|
| 4,024,588 A * | 5/1977 | Janssen et al. ............ 623/18.12 |
| 4,045,825 A | 9/1977 | Stroot | |
| 4,675,670 A | 6/1987 | Lalonde et al. | |
| 4,950,986 A * | 8/1990 | Guerrero ............... 324/207.19 |
| 5,113,869 A | 5/1992 | Nappholz et al. | |
| 5,197,488 A | 3/1993 | Kovacevic | |
| 5,300,120 A | 4/1994 | Knapp et al. | |
| 5,360,016 A | 11/1994 | Kovacevic | |
| 5,376,128 A | 12/1994 | Bozeman | |
| 5,395,033 A | 3/1995 | Byrne et al. | |
| 5,458,655 A | 10/1995 | Bozeman | |

(Continued)

FOREIGN PATENT DOCUMENTS

WO    WO 00/65981    11/2000

(Continued)

OTHER PUBLICATIONS

European Search Report for European Application No. 05251832.1-2310 PCT/ dated Aug. 5, 2005, 4 pages.

(Continued)

*Primary Examiner*—Pedro Philogene

(57) ABSTRACT

A joint endoprosthesis system has first and second prosthetic components. The second prosthetic component has a bearing surface. The interface of the bearing surface and the first prosthetic component defines the joint articulation. A signal source and sensor are affixed on opposite sides of the joint articulation. The signal source generates a first signal that is received by the sensor. The sensor generates a second signal that has a characteristic that varies depending on the distance between the sensor and the signal source. A transmitter transmits a signal. The signal has a characteristic that varies depending on the characteristic of the second signal. This system can be used to measure a dimension of the joint space and to determine whether a dimension of the joint space has changed over time. The system may alternatively use magnets and magnetic sensors.

43 Claims, 23 Drawing Sheets

U.S. PATENT DOCUMENTS

| | | | |
|---|---|---|---|
| 5,465,619 A | 11/1995 | Sotack et al. | |
| 5,470,354 A | 11/1995 | Hershberger et al. | |
| 5,480,454 A | 1/1996 | Bozeman | |
| 5,518,008 A | 5/1996 | Cucchiaro et al. | |
| 5,609,643 A | 3/1997 | Colleran et al. | |
| 5,769,875 A | 6/1998 | Peckham et al. | |
| 5,776,171 A | 7/1998 | Peckham et al. | |
| 5,831,430 A | 11/1998 | Pfanstiehl et al. | |
| 5,935,171 A * | 8/1999 | Schneider et al. | 623/22.15 |
| 5,954,758 A | 9/1999 | Peckham et al. | |
| 6,026,328 A | 2/2000 | Peckham et al. | |
| 6,155,267 A | 12/2000 | Nelson | |
| 6,163,725 A | 12/2000 | Peckham et al. | |
| 6,228,900 B1 | 5/2001 | Shen et al. | |
| 6,245,109 B1 * | 6/2001 | Mendes et al. | 623/18.11 |
| 6,272,379 B1 | 8/2001 | Fischell et al. | |
| 6,281,264 B1 | 8/2001 | Salovey et al. | |
| 6,281,679 B1 | 8/2001 | King et al. | |
| 6,332,089 B1 | 12/2001 | Acker et al. | |
| 6,400,989 B1 | 6/2002 | Eckmiller | |
| 6,402,689 B1 | 6/2002 | Scarantino et al. | |
| 6,442,413 B1 | 8/2002 | Silver | |
| 6,447,448 B1 | 9/2002 | Ishikawa et al. | |
| 6,454,781 B1 | 9/2002 | Witt et al. | |
| 6,473,652 B1 | 10/2002 | Sarwa et al. | |
| 6,498,944 B1 | 12/2002 | Ben-Haim et al. | |
| 6,506,216 B1 | 1/2003 | McCue et al. | |
| 6,507,189 B2 | 1/2003 | Woolsey et al. | |
| 6,558,229 B2 | 5/2003 | Kimura et al. | |
| 6,563,308 B2 | 5/2003 | Nagano et al. | |
| 6,573,706 B2 * | 6/2003 | Mendes et al. | 324/207.17 |
| 6,583,630 B2 | 6/2003 | Mendes et al. | |
| 6,679,920 B2 | 1/2004 | Biedermann et al. | |
| 6,689,056 B1 | 2/2004 | Kilcoyne et al. | |
| 6,890,303 B2 | 5/2005 | Fitz | |
| 6,917,831 B2 | 7/2005 | Bloemer et al. | |
| 2001/0000187 A1 | 4/2001 | Peckham et al. | |
| 2002/0133175 A1 | 9/2002 | Carson | |
| 2002/0147455 A1 | 10/2002 | Carson | |
| 2003/0069644 A1 | 4/2003 | Kovacevic et al. | |
| 2004/0019384 A1 | 1/2004 | Kirking et al. | |
| 2004/0034355 A1 | 2/2004 | Govari et al. | |
| 2004/0243148 A1 | 12/2004 | Wasielewski | |

FOREIGN PATENT DOCUMENTS

WO    WO 2005/055871 A    6/2005

OTHER PUBLICATIONS

Bhadra, Niloy, M.D., et al; Implementation of an Implantable Joint-Angle Transducer (2002). J. Rehab Res Dev, 39(3).

Graichen, F., et al; Four-Channel Telemetry System for In Vivo Measurement of Hip Joint Forces (1991). J. Biomed. Eng. 1991, vol. 13, Sep.

Graichen, F., et al; Inductively Powered Telemetry System for In Vivo Measurement With Orthopaedic Implants (1995); Biotelemetry XIII, Mar. 26-31, 1995—Williamsburg, VA.

Johnson, Mark W., et al; Implantable Transducer for Two-Degree of Freedom Joint Angle Sensing (1999). IEEE Trans Rehab Eng, pp. 349-359 7(3).

Miller, Joel S., et al; Molecule-Based Magnets-An Overview (2000). MRS Bulletin, Nov.

Seedhom, B.B., et al; A Technique for the Study of Geometry and Contact in Normal and Artificial Knee Joints (1972). Wear—Elsevier Sequoia S.A., Lausanne—Printed in the Netherlands.

Troyk, Philip R., et al; Design and Implementation of an Implantable Goniometer (1986); IEEE Transactions on Biomedical Engineering, vol. BME-33, No. 2, Feb.

Bhadra, N., MD, et al; Implementation of an implantable joint-angle transducer, Journal of Rehabilitation Research and Development, May/Jun. 2002, pp. 411-422, vol. 39, No. 3.

Bragdon, C.R., et al; Experimental assessment of precision and accuracy of radiostereometric analysis for the determination of polyethylene wear in a total hip replacement model. Journal of Orthopaedic Research, 2002, pp. 688-695, 20.

Cicuttini, F. M., et al; Tibial and femoral cartilage changes in knee osteoarthritis. Ann Rheum Dis Oct. 2001; pp. 977-980, 60.

Conrozier, T., et al; Quantitative radiography in osteoarthritis: Computerized measurement of radiographic knee and hip joint space. Bailliere's Clinical Rheumatology, Aug. 1996, pp. 429-433, vol. 10, No. 3.

Hilliquin, P., et al; Quantitative assessment of joint space width with an electronic caliper; Osteoarthritis and Cartilage Jul. 2002; pp. 542-546, 10.

Hyldahl, H.C., MD, et al; Does Metal Backing Improve Fixation of Tibial Component in Unicondylar Knee Arthroplasty? A Randomized Radiostereometric Analysis. The Journal of Arthroplasty, 2001, pp. 174-179, vol 16 No. 2.

Ilchmann, T., Thesis Radiographic assessment of cup migration and wear after hip replacement. Acta Orthopaedica Scandinavica, Oct. 1997, vol. 68, No. 276.

Johnson, M.W., et al; Implantable Transducer for Two-Degree of Freedom Joint Angle Sensing, IEEE Transactions on Rehabilitation Engineering, Sep. 1999, pp. 349-359, vol. 7, No. 3.

Karrholm, J., MD, et al; Radiostereometry of Hip Prostheses Review of Methodology and Clinical Results, Clinical Results, Clinical Orthopaedics and Related Research, 1997, pp. 94-110 No. 344.

Lanyon, P., et al; Radiographic assessment of symptomatic knee osteoarthritis in the community: definitions and normal joint space. Ann Rheum Dis 1998, pp. 595-601 No. 57.

Onsten I, et al; Wear in uncemeneted porous and cemented polyethylene sockets: A Randomised, Radiosterometric Study. The Journal of Bone and Joint Surgery Br, Mar. 1998; pp. 345-350, 80(2).

Pavelka, K., et al; Correlation between knee roentgenogram changes and clinical symptoms in osteoarthritis. Rev. Rhum. Mal. Osteoartic., 1992, pp. 553-559, 59 (9).

Ryd, L., et al; Methods for determining the accuracy of radiostereometric analysis (RSA), Acta Orthopaedic Scandinavica, 2000, pp. 403-408, 71 (4).

Selvik, G., Roentgen stereophotogrammetry A method for the study of the kinematics of the skeletal system. Acta Orthopaedica Scandinavica, 1989, vol. 60, No. 232, Munksgaard Copenhagen.

Sychterz, Christi J., MS, et al; Effect of Radiographic Quality on Computer-Assisted Head Penetration Measurements. Clinical Orthopaedics and Related Research, 2001, pp. 150-158, No. 386.

Vrooman, H,A., et al; Fast and accurate automated measurements in digitized stereophotogrammetric radiographs. Journal of Biomechanics, 1998, pp. 491-498, 31.

* cited by examiner

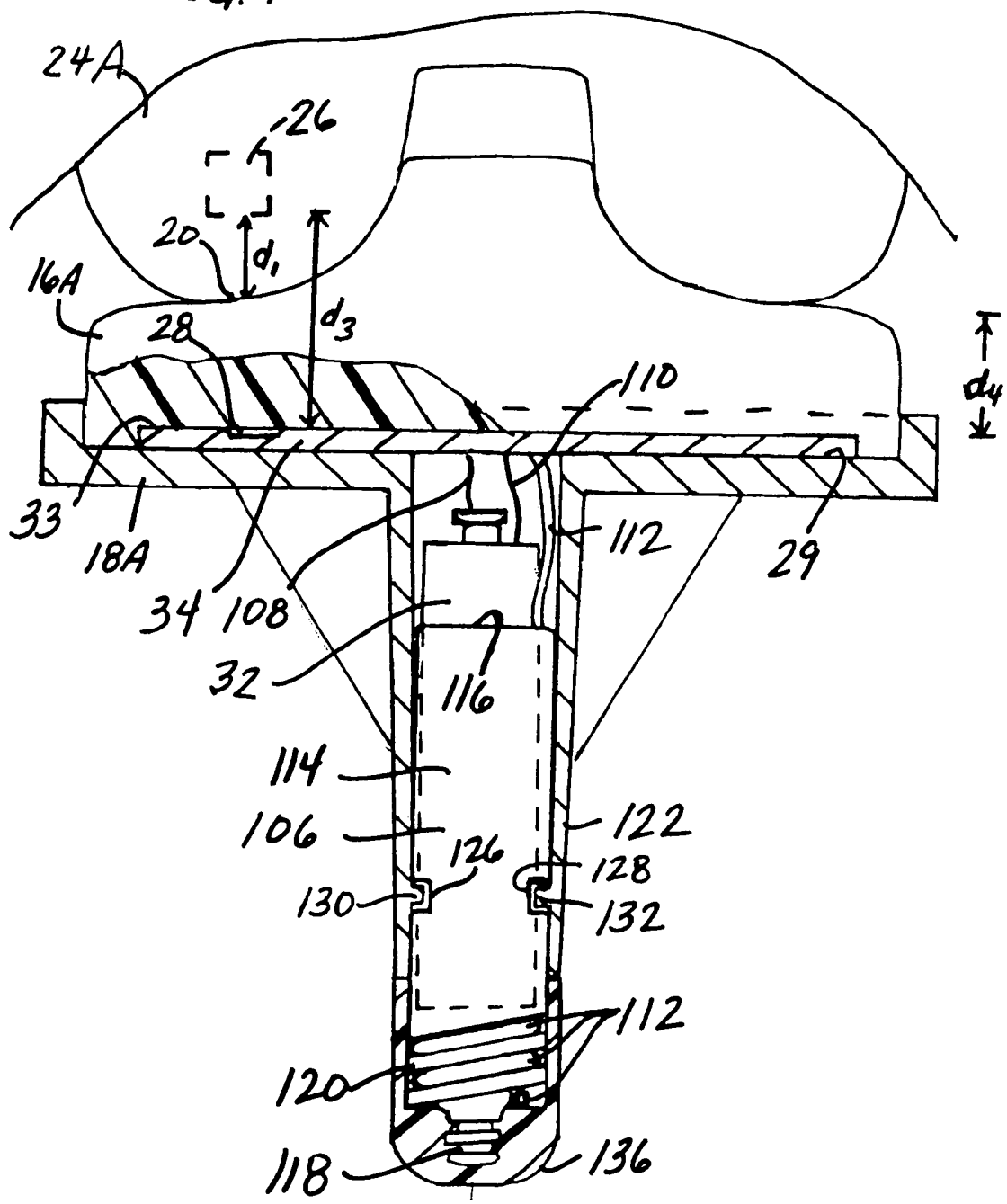

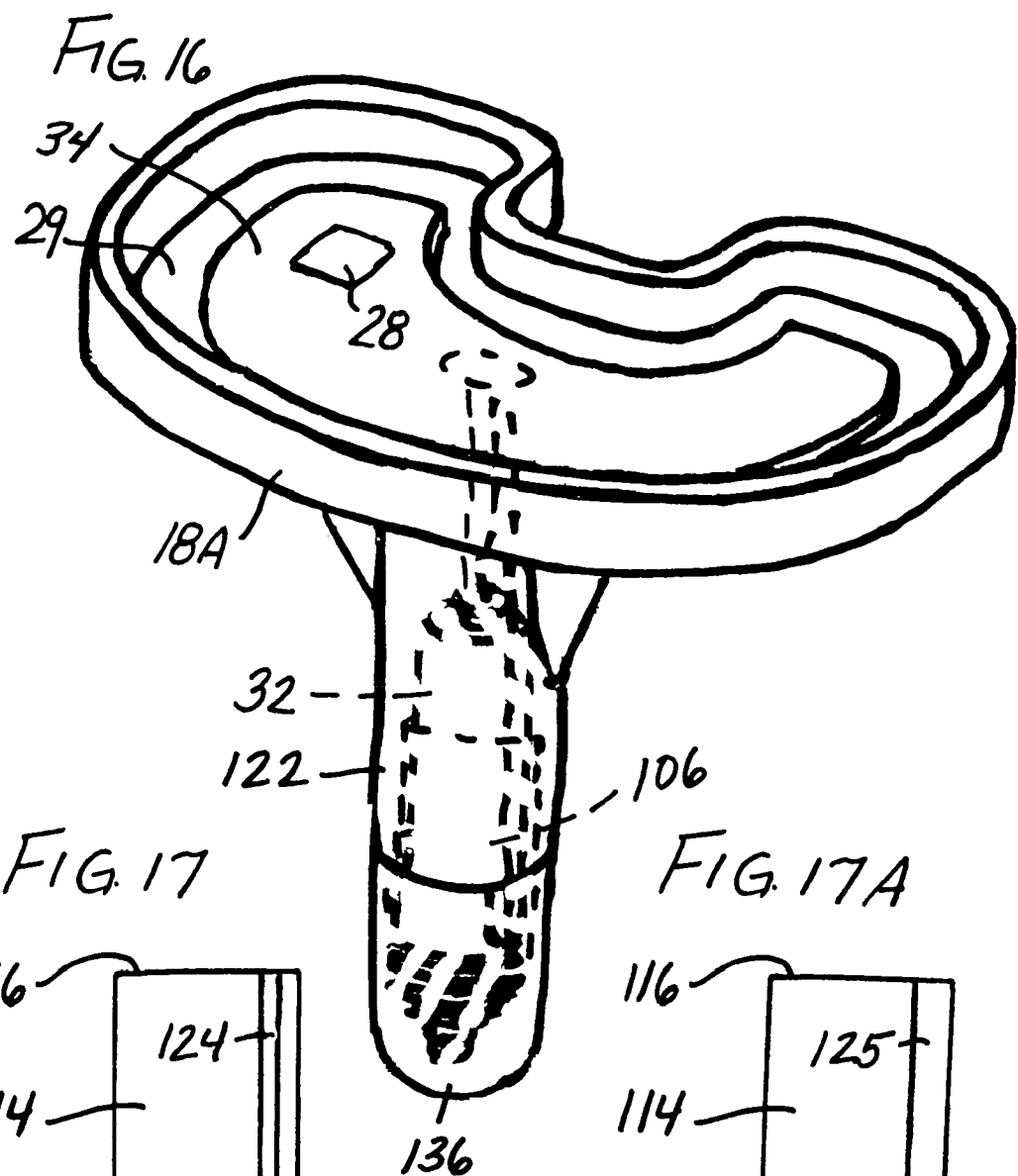

IN VIVO JOINT SPACE MEASUREMENT DEVICE AND METHOD

CROSS-REFERENCE TO RELATED APPLICATIONS

This application claims priority to U.S. Provisional Application Ser. No. 60/486,615 filed on Jul. 11, 2003 by Mark R. DiSilvestro, entitled "In Vivo Joint Space Measurement Device and Method," which is incorporated by reference herein in its entirety.

FIELD OF THE INVENTION

The present invention relates to joint endoprostheses systems.

BACKGROUND OF THE INVENTION

Human joints can become damaged as a result of accident or illness. Such damage can be, for example, to the articular cartilage covering the ends of the bones at the joint as well as the intra-articular cartilage between the ends of the adjacent bones of the joint. When the damage to the joint is severe, a joint endoprosthesis can be implanted to improve the comfort and mobility of the patient.

Joint endoprostheses have been developed to replace native tissue of several human joints. There are a variety of knee prostheses, hip prostheses, shoulder prostheses, ankle prostheses, elbow prostheses, wrist prostheses and finger prostheses available to relieve patient suffering. Such devices are available, for example, from DePuy Orthopaedics, Inc. (DePuy Products, Inc.) of Warsaw, Ind.

Standard joint endoprostheses include components that are affixed to the articulating ends of the bones of the joint and commonly include a bearing component positioned in the joint space between the bone-affixed components. Standard bearing components of joint endoprostheses have a surface against which one of the bone-affixed components articulates. For example, hip endoprostheses include a proximal femoral component to be affixed to the proximal femur and an acetabular cup or shell to be affixed to the acetabulum. Many of these standard hip endoprostheses include a liner in the acetabular cup against which the head of the proximal femoral component articulates. Knee prostheses commonly include a distal femoral component to be affixed to the distal femur and a proximal tibial component to be affixed to the proximal tibia. Tibial bearings are typically in the joint space between the femoral and tibial components, carried by the tibial component. Similar systems with bearings are available to replace other joints in the body.

Standard bearings for joint endoprostheses are made of ultrahigh molecular weight polyethylene (UHMWPE), ceramic and metal. Bearing wear is problematic in the orthopaedic field. Several patents have addressed the problem particles produced by UHMWPE wear, and the association of these wear particles with osteolysis. See, for example: U.S. Pat. No. 6,281,264, "Chemically Crosslinked Ultrahigh Molecular Weight Polyethylene for Artificial Human Joints" and U.S. Pat. No. 6,228,900 "Crosslinking of Polyethylene for Low Wear Using Radiation and Thermal Treatments." In addition, the bearing can wear in an uneven manner if the soft tissue of the joint is or becomes unbalanced. For example, if the soft tissue of the knee is unbalanced, the medial or lateral side of the tibial bearing could be subjected to additional stress and wear.

Osteolysis at the site of the orthopaedic implant is associated with loosening of the components of the joint endoprosthesis. Such loosening of the components can require a revision surgery, wherein the original joint endoprosthesis components are removed and replaced.

Orthopaedic surgeons have monitored the condition of the joint space occupied by bearings to monitor the condition of the patient. Typically, narrowing of the joint space has been monitored from measurements taken from radiographs or by use of radio stereophotogrammetric analysis (RSA). Both methods require use of external imaging devices, and both can be time consuming. Both methods are prone to some measurement error due to the limited accuracy of the equipment. Also, the accuracy of measurements of joint space taken from radiographs depends on analysis technique and bias, affecting repeatability and reproducibility. In addition, because of the high equipment cost, it is unlikely that RSA will become a standard technique in patient monitoring.

Early detection of bearing wear could find use as a signal to the orthopaedic surgeon that some type of intervention is needed before the condition degenerates to the point of requiring revision surgery. For example, the surgeon may determine that the patient needs to make some lifestyle changes if revision is to be postponed. Moreover, if therapeutic agents to treat early stage osteolysis are available, these agents could be administered before the condition degenerates to the point where revision surgery is necessary.

Reference is made to the following United States patents, the disclosures of which are incorporated by reference herein in their entireties: U.S. Pat. No. 6,583,630 to Mendes et al. entitled "Systems and Methods for Monitoring Wear and/or Displacement of Artificial Joint Members, Vertebrae, Segments of Fractured Bones and Dental Implants"; U.S. Pat. No. 6,573,706 to Mendes et al. entitled "Method and Apparatus for Distance Based Detection of Wear and the Like in Joint"; and U.S. Pat. No. 6,245,109 to Mendes et al. entitled "Artificial Joint System and Method Utilizing Same for Monitoring Wear and Displacement of Artificial Joint Members."

SUMMARY OF THE INVENTION

The present invention addresses the need to provide readily accessible and accurate data for monitoring the condition of joint endoprostheses.

In one aspect, the present invention provides a joint endoprosthesis system for use in a joint comprising two bones interfacing at a joint articulation in a patient's body. The joint endoprosthesis system comprises a first prosthetic component to be affixed to one bone of the joint and a bearing component to be positioned adjacent to the first prosthetic component at the joint articulation. The joint endoprosthesis system also includes a signal source to be affixed within the patient's body on one side of the joint articulation. The signal source serves to generate a first signal. The joint endoprosthesis system also includes a distance reference and an internal transmitter. The distance reference is to be affixed in the patient's body across the joint articulation from the signal source and an internal transmitter. The internal transmitter is to be affixed within the patient's body. The internal transmitter is capable of producing a transmitter signal that has a characteristic that varies depending on the distance between the signal source and the distance reference. The transmitter signal that is produced by the internal transmitter is also capable of being transmitted from within the patient's body to a location outside of the patient's body.

In another aspect, the present invention provides a method of determining a dimension of a joint space in the body of a patient wherein the patient has a joint endoprosthesis that includes a first prosthetic component affixed to one bone of the joint, and a bearing occupying the joint space adjacent to the first prosthetic component. The method comprises generating a distance-related signal that has a characteristic that relates to a dimension of the joint space. Another signal is transmitted from within the patient's body to a location outside of the patient's body. The signal transmitted outside of the patient's body has a characteristic that relates to the characteristic of the distance-related signal. A dimension of the joint space is determined based on the value of the characteristic of the signal transmitted to the external location.

In another aspect, the present invention provides a method of determining a change in a dimension of a joint space in the body of a patient wherein the patient has a joint endoprosthesis that includes a first prosthetic component affixed to one bone of the joint and a bearing occupying the joint space adjacent to the first prosthetic component. The method comprises generating a first signal from one side of the joint space at a first location within the patient's body. The first signal is received on the opposite side of the joint space at a second location within the patient's body. Another signal is transmitted from a location within the patient's body to an external location. The signal transmitted to the external location has a characteristic that relates to distance between the first location and the second location. The extent of change in a dimension of the joint space is determined based on the characteristic of the signal transmitted to the external location.

In another aspect, the present invention provides an implantable medical device comprising a material that acts selectively as a magnet.

In another aspect, the present invention provides a medical system comprising an implantable prosthetic component, a material that acts selectively as a magnet carried by the implantable prosthetic component and an external sensor for sensing a characteristic produced by the material that acts selectively as a magnet.

In another aspect, the present invention provides a joint endoprosthesis system for use in a joint comprising two bones interfacing at a joint articulation in a patient's body. The joint endoprosthesis system comprises first and second prosthetic components, a magnet and a sensor. The second prosthetic component has a bearing surface to be placed against the first prosthetic component. The interface of the first prosthetic component and the bearing surface of the second prosthetic component defines a joint articulation. The magnet is to be affixed within the patient's body. The sensor is to be maintained outside of the patient's body. The sensor is capable of sensing a property of the magnetic field of the magnet.

BRIEF DESCRIPTION OF THE DRAWINGS

FIG. 15 is an anterior/posterior elevation of the components of another embodiment of a knee endoprosthesis system, with the tibial tray, end cap and a portion of the tibial bearing shown in cross-section;

FIG. 16 is a perspective view of the tibial tray component of FIG. 15;

FIG. 17 is an elevation of the positioner of FIGS. 15–16;

FIG. 17A is an elevation of the positioner of FIGS. 15–16;

DETAILED DESCRIPTION OF THE ILLUSTRATED EMBODIMENTS

Figure 12:
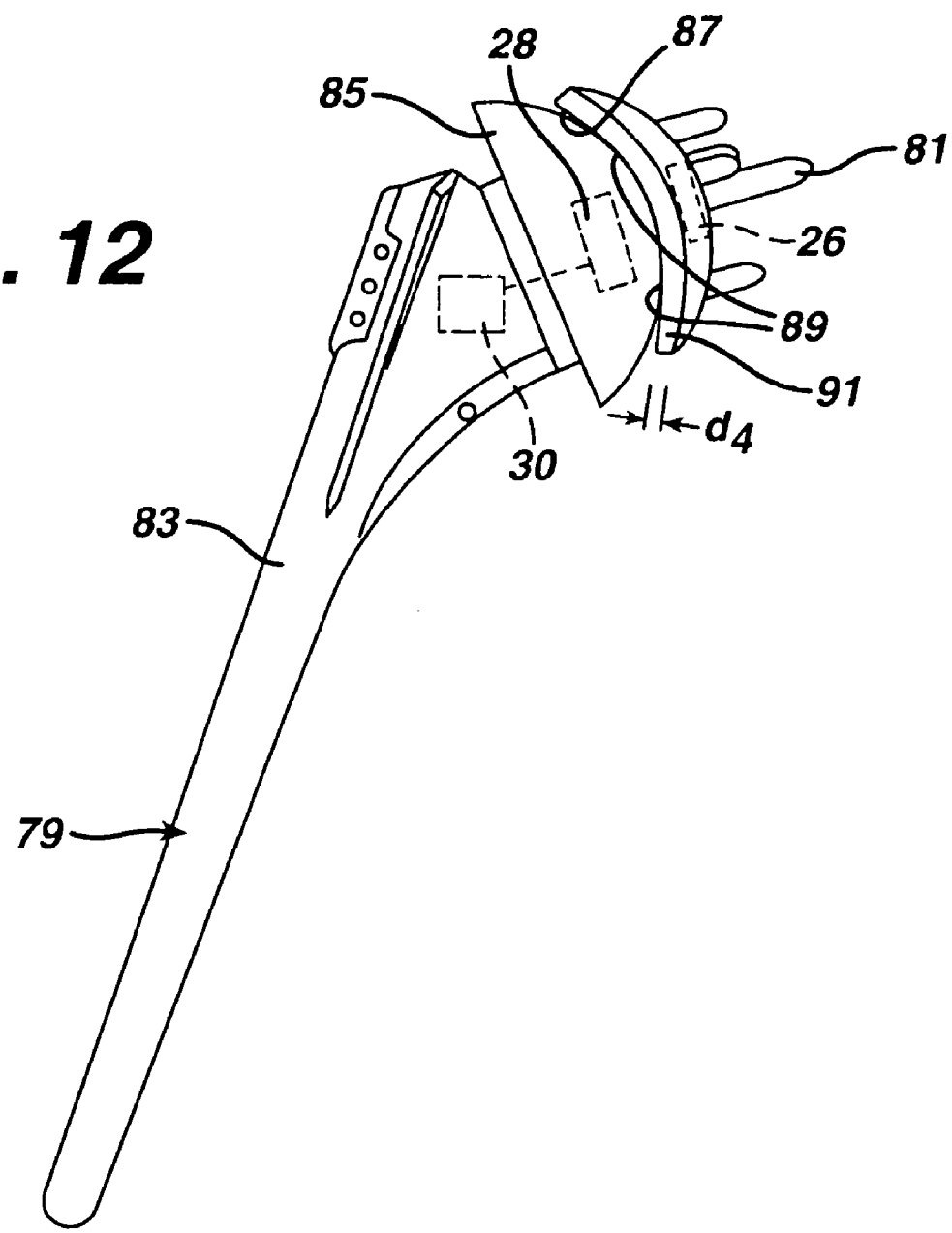
FIG. 12 is an anterior/posterior elevation of the components of a shoulder endoprosthesis system.

Joint endoprosthesis systems incorporating the principles of the present invention are illustrated in the accompanying drawings. In FIGS. 1, 4, 6, 8, 10, 15 and 16, the system is a knee endoprosthesis system. In FIG. 7, the system is a hip endoprosthesis system. In FIG. 12, the system is a shoulder endoprosthesis system. It should be understood that FIGS. 1, 4, 6–8, 12 and 15–16 are diagrammatic illustrations of these systems and components, and do not depict all of the features of the prosthetic components. It should also be understood that the teachings of the present invention can also be applied to other joint endoprostheses, including elbow, wrist, and ankle endoprostheses and endoprostheses for use with the digits of the extremities.

Each of the illustrated knee endoprosthesis and hip endoprosthesis systems includes three basic components: a first prosthetic component to be affixed to one bone of the joint, a second prosthetic component to be affixed to the other bone of the joint, and a bearing to be positioned at the joint articulation, in the joint space adjacent to one of the bone-affixed components. In the knee endoprosthesis system, the first component comprises a distal femoral component with condyles defining an articulating surface. The second component comprises a proximal tibial component. The bearing is a tibial bearing carried by the tibial component. The tibial bearing has an upper surface bearing against the condyles of the distal femoral component. The interface of the condyles of the distal femoral component and the upper surface of the tibial bearing defines the articulation of the knee prosthesis system. The tibial bearing occupies the joint space between the distal femoral and proximal tibial components, and the thickness of the tibial bearing corresponds with the thickness of the joint space in the knee endoprosthesis system. In the hip prosthesis system, the first component comprises an acetabular cup or shell to be affixed to a prepared space in the patient's acetabulum. The second component comprises a proximal femoral component. The proximal femoral component has a femoral head defining an articulating surface. The bearing is an acetabular liner carried by the acetabular cup. The acetabular liner has a curved surface bearing against the femoral head of the proximal femoral component. The interface of the femoral head and the curved surface of the acetabular liner defines the articulation of the hip prosthesis system. The acetabular liner occupies the joint space between the acetabular cup and the femoral head, and the thickness of the acetabular liner corresponds with the thickness of the joint space of the hip endoprosthesis system. Analogous components are present in other joint endoprosthesis systems.

The illustrated shoulder endoprosthesis system includes two basic components. The first component comprises a humeral component, including a stem and a humeral head. The second component comprises a glenoid component. The surface of the humeral head defines an articulating surface. The glenoid component has a surface that bears against the humeral head. The interface of the humeral head and the glenoid component defines the articulation of the shoulder joint prosthesis system. A portion of the glenoid component occupies the joint space, and the thickness of this portion of the glenoid component corresponds with the thickness of the joint space of the shoulder endoprosthesis system. Thus, a portion of the glenoid component comprises a bearing and a portion of the glenoid component is affixed to bone.

The femoral, tibial and bearing components for the knee endoprosthesis system can have features of known commercially available knee endoprosthesis systems, such as those made by and available from DePuy Products, Inc. and DePuy Orthopaedics, Inc. of Warsaw, Ind. Similarly, the femoral, acetabular and bearing components for the hip endoprosthesis system can have features of known commercially available hip systems, such as those available from DePuy Orthopaedics, Inc. of Warsaw, Ind. The humeral and glenoid components of the shoulder endoprosthesis system of the present invention can also have features of known commercially available shoulder systems, such as those available from DePuy Orthopaedics, Inc. of Warsaw, Ind. The components of these systems can also have features of the commercially available products of other suppliers of knee, hip and shoulder endoprostheses, such as those available from Zimmer, Inc. of Warsaw, Ind., Biomet, Inc. of Warsaw, Ind., Stryker Howmedica Osteonics, Inc. of Mahwah, N.J., and Smith & Nephew, Inc. of Memphis, Tenn. It should be understood that it is anticipated that the endoprosthesis systems of the present invention may include subsequent improvements to these commercial products. It should also be understood that although standard materials such as cobalt chrome, titanium, polyethylene, and ceramics, can be used for these components of the joint endoprostheses, the present invention is not limited to any particular material for any of the components unless expressly set forth in the claims.

The endoprosthesis systems of the present invention include a signal source, a distance reference and associated electronics that provide data for determining the size of a joint space so that the orthopaedic surgeon can determine whether wear has occurred between articulating components of the endoprosthesis and the extent of such wear.

As used herein, "signal" is intended to encompass fields, such as magnetic and electric fields, flux densities, currents and waves such as acoustic waves and radio-frequency waves, for example. "Signal source" is intended to encompass devices such as permanent magnets, paramagnetic and superparamagnetic materials, and electronic circuits that produce such signals. Accordingly, "signal" and "signal source" should not be limited to a particular type of signal or signal source unless expressly called for in the claims.

In the illustrated embodiments, the signal source serves to generate a first signal. If the signal source is a permanent magnet, paramagnet or superparamagnet, the signal generated is a magnetic field or a magnetic flux density. If the signal source is a radio-frequency (RF) transmitter, the signal generated comprises radio-frequency waves. Other types of electronic signal sources could serve to generate eddy currents or an electric field. These signals are referred to as the "first signal" herein. The first signal may have a characteristic that varies with distance from the signal source; for example, the strength of the magnetic field decreases as the distance from the magnet increases.

As used herein, "distance reference" is intended to encompass both sensors and targets.

"Sensor" is intended to encompass devices such as transducers, transponders, and electromagnetic sensors. The sensor functions to sense the distance-varying characteristic of the first signal generated by the signal source. For example, the sensor may function to sense the magnitude of the flux density generated by a permanent magnet at a particular location, or may function to sense the frequency, amplitude or phase of an RF wave generated by an RF transmitter. The sensor may also serve to generate a second signal that has a characteristic that varies depending on some characteristic of the first signal it has sensed. The signal source and sensor can be part of a single common element.

"Target" is intended to include a component in which eddy currents or electrical charges are induced. In the case of a joint endoprosthesis system, the target can comprise a surface or portion of a surface of one of the metal components, such as the proximal surface of the proximal tibial component or the distal surface of the condyles of the distal femoral component.

Generally, in most of the illustrated embodiments, the signal source is positioned on one side of the articulation or joint space of the joint endoprosthesis and the distance reference (sensor or target) is positioned on the opposite side of the articulation or joint space of the joint endoprosthesis. The signal source is at a fixed position with respect to one of the endoprosthesis components and the distance reference is at a fixed position with respect to the other endoprosthesis component on the opposite side of the joint space occupied by the bearing element. Since the positions of the signal source and distance reference are fixed with respect to the bone-affixed components of the joint endoprosthesis, changes in the relative positions of the signal source and distance reference correspond with changes in the joint space (and also potentially with migration or subsidence of the implant components with respect to the bones), that is, with changes in the thickness of the bearings occupying the joint space. Thus, if the distance between the signal source and distance reference decreases over time, this decrease in distance corresponds with a decrease in the thickness of the bearing component or bearing portion of a component, indicating that the bearing has worn and providing an accurate measurement of the extent of such wear.

Changes in the relative position of the implant components on both sides of the joint space can also be determined by including signal sources on both sides of the joint space within the body and distance references at at least two additional locations, such as at external locations. The distance between each signal source and the distance reference can be used to determine changes in the joint space. Details of this method of determining changes in the joint space are described in more detail below with respect to the embodiment of FIGS. 24–25.

Figure 1:
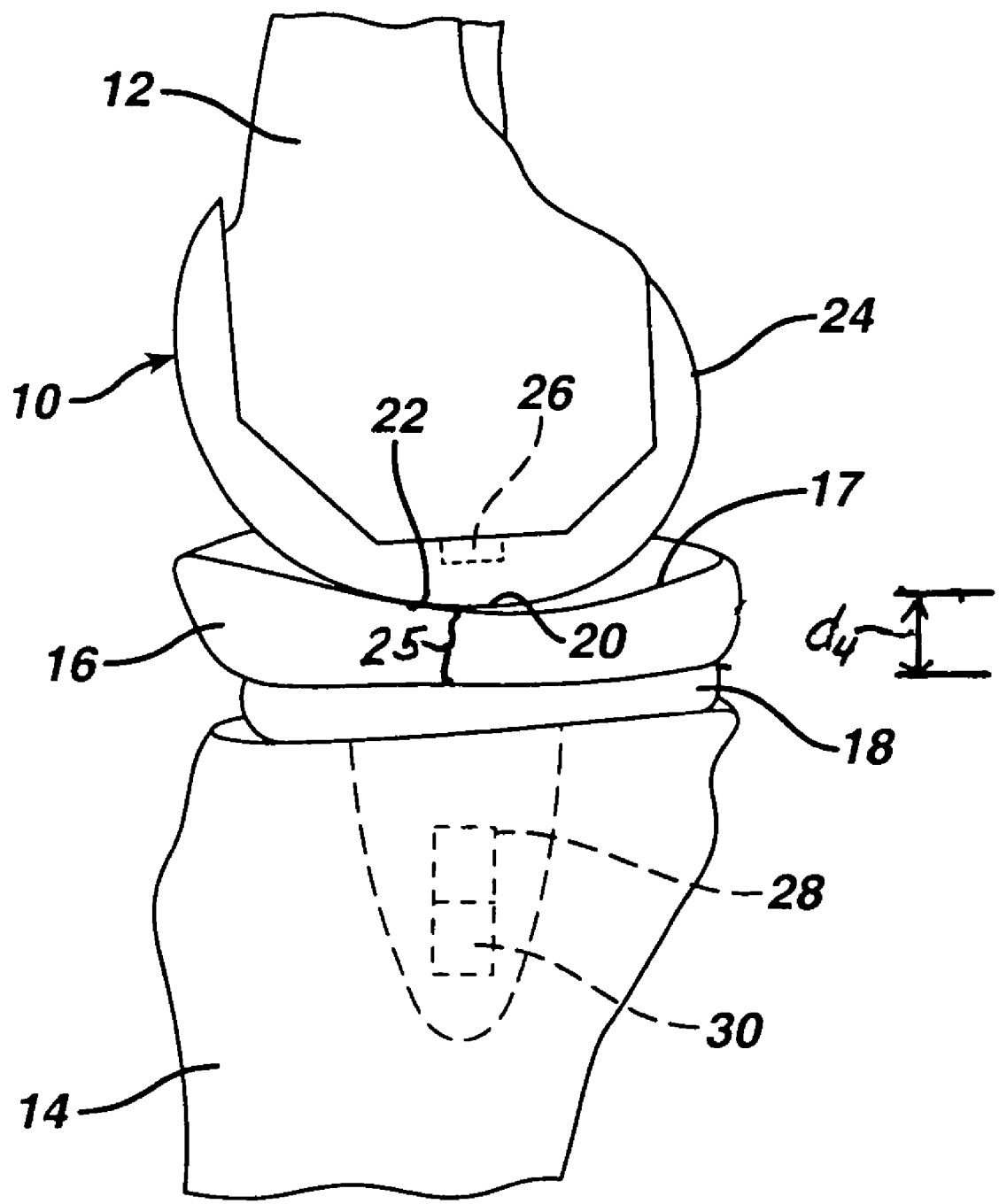
FIG. 1 is a medial/lateral elevation of a first embodiment of a knee endoprosthesis system with the distal femoral component affixed to the distal femur and the proximal tibial component affixed to the proximal tibia, showing the knee joint in extension.

Referring now to the embodiment of FIG. 1, a knee endoprosthesis system 10 is illustrated implanted on the distal end of a femur 12 and proximal end of a tibia 14. The illustrated system 10 includes a tibial bearing 16 that is carried by the proximal tibial component 18. The tibial bearing 16 has a contoured proximal surface 17, against which the condyles 22 of the distal femoral component 24 bear. Articulation of the joint is at the interface of the proximal surface 17 of the tibial bearing 16 and the condyles 22 of the distal femoral component 24. The joint articulation is indicated at 20 in FIG. 1. The tibial bearing 16 occupies the joint space between the opposing bone-affixed components 18, 24; the joint space is indicated at 25 in FIG. 1. The thickness of the tibial bearing 16 and of the joint space is indicated at $d_4$ in FIG. 1.

The tibial bearing 16, proximal tibial component 18 and distal femoral component 24 can all be made of standard materials for such parts. It is anticipated that the principles of the present invention will also be applicable if these components 16, 18, 24 are made of different or new materials.

In the embodiment of FIG. 1, the signal source 26 comprises a permanent magnet. In this first illustrated embodiment, the signal source 26 (permanent magnet) is affixed to the distal femoral component 24 along one of the interior surfaces of the component, such as in a receptacle or recess of complementary shape formed in the distal femoral component. In FIG. 1, the signal source 26 is shown in phantom. Thus, the signal source 26 is at a fixed, known distance from the articulating surfaces of the condyles 22 of the distal femoral component 24. A suitable commercially-available permanent neodymium magnet is available from Ogallala Electronics Division, Ogallala, Nebr. of the Arnold Engineering group of SPS Technologies, Inc. of Jenkintown, Pa., for example. However, it should be understood that the present invention is not limited to use of any particular type of magnet or to the use of a magnet as the signal source, unless expressly called for in the claims; for example, if a magnetic field is to be used for distance measurement, the signal source could comprise a material that selectively acts as a magnet. For example, a paramagnetic or superparamagnetic material could be used as the signal source. Superparamagnetic materials typically contain ferrite or a similar iron oxide compound encased or distributed in a polymer. The metal compound is usually provided in the form of very small magnetic particles, such as microspheres (below about 100–150 nm) which, because their size is under a critical value, do not behave any longer as small autonomous magnets, that is, they will align in a preferential direction only when subjected to an external magnetic field. Use of a superparamagnetic material as the signal source 26 is anticipated to be useful in that the material should be compatible with magnetic resonance imaging and does not retain magnetization unless subjected to selected conditions. Utilization of superparamagnets as signal sources is described in more detail below with respect to the embodiment of FIGS. 24–25. Unless otherwise expressly limited, the term "magnet" should be interpreted to include a permanent magnet, a paramagnet and a superparamagnet. The expression "material that acts selectively as a magnet" should be interpreted to mean materials such as paramagnets and superparamagnets.

The distance reference in the embodiment of FIG. 1 comprises a sensor 28. In this particular embodiment, the sensor 28 is a Hall effect transducer affixed to the proximal tibial component 18 at a position spaced from the tibial bearing 16. A Hall effect transducer produces an electrical signal in response to the magnetic flux density generated by the magnet. The magnitude of the magnetic flux density (first signal) varies with the distance from the magnet, and the magnitude of the voltage (second signal) produced by the Hall effect transducer varies with the magnitude of the magnetic flux density (first signal) created by the magnet. Thus, magnitude or value of the voltage (second signal) produced by the sensor 28 provides a measurement of the distance between the sensor 28 and the signal source 26. Accuracy on the order of 0.001 mm can be achieved using the magnet and Hall effect transducer of the illustrated knee prosthesis system as the signal source 26 and sensor 28.

A suitable Hall effect transducer is commercially available from Allegro Microsystems of Hillsborough, N.C. and is identified as a Ratiometric Linear Hall Effect sensor, part UGN3503LT. It should be understood that this transducer is identified as an example only; the present invention is not limited to use of any particular Hall effect transducer. In addition, there are three-dimensional Hall effect sensors or tranducers that can be used to compensate for implant subsidence or migration; an example of such a three-dimensional Hall effect transducer or sensor is disclosed by Ch. Schott and R. S. Popovic in "Integrated 3-D Hall Magnetic Field Sensor", EPFL—Swiss Fed. Inst. of Technology, EPFL-BM, CH-1015, Lausanne, Switzerland, (presented at the 10$^{th}$ International Conf. on Solid State Sensors and Activators, Jun. 7–10, 1999, Transducers '99, Sendai, Japan). In addition, other magnetic field sensitive elements, such as a magnetoresistive element or a magnetic transistor, are anticipated to be useful as the sensor 28 of the present invention. Moreover, the present invention is not limited to use of a transducer as the sensor. The sensor could comprise other elements, such as an RF receiver, for example, as described in more detail below.

Figure 2:
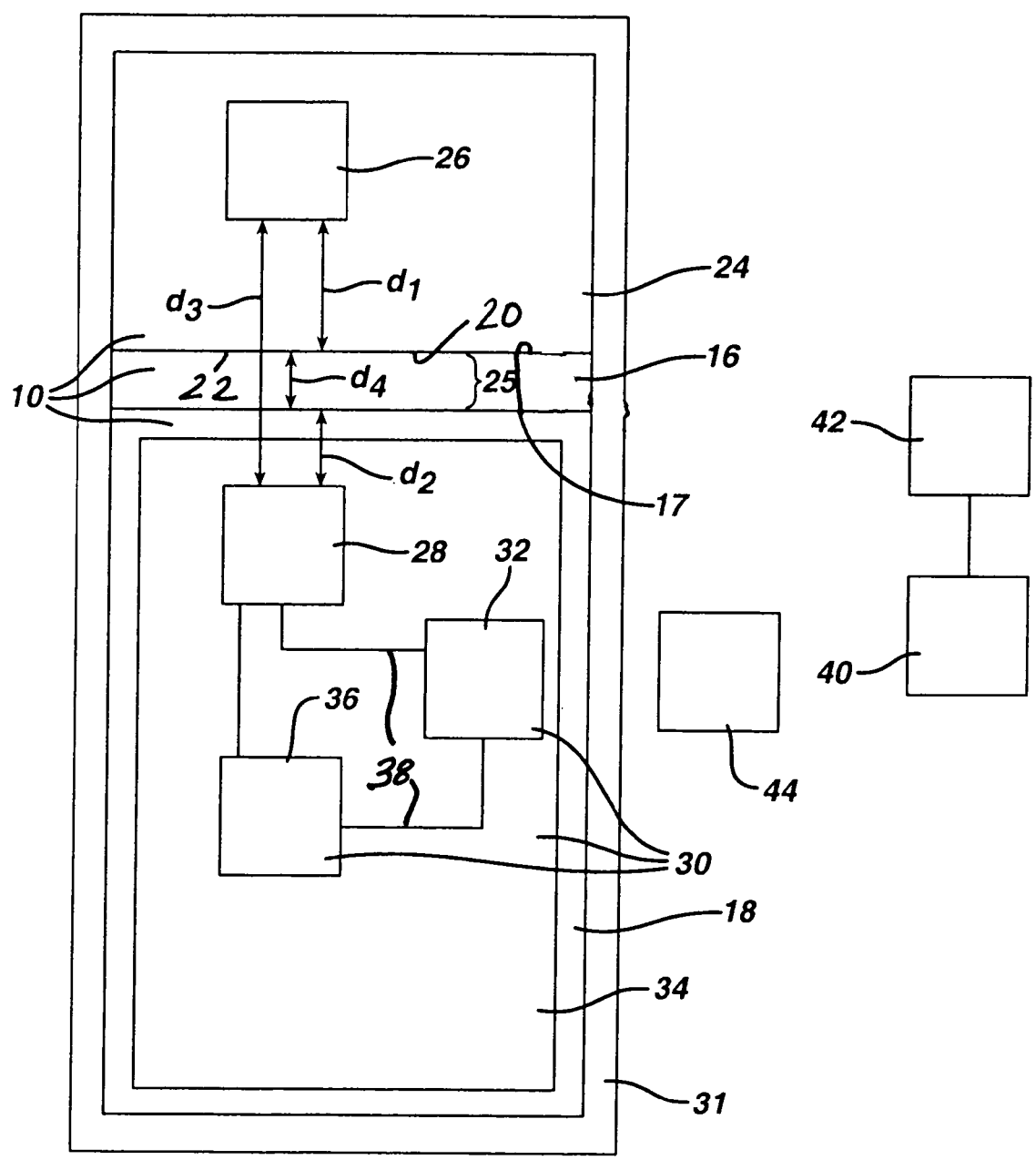
FIG. 2 is a schematic illustration of the knee endoprosthesis system of FIG. 1, showing external components of the system in addition to those implanted in the patient.

FIG. 2 illustrates the principles of the first embodiment of the present invention schematically. As shown therein, the patient's body is represented by the large box labeled 31. The magnet that serves as the signal source 26 is illustrated as a component of the distal femoral component 24. The Hall effect transducer that serves as the sensor 28 is illustrated as a component of the proximal tibial component 18. The tibial bearing 16 is shown schematically between the femoral and tibial components 24, 18.

As shown schematically in FIG. 2, the knee endoprosthesis system 10 includes implanted electronic components 30. These electronic components 30 include a power component 32, a printed circuit board 34, a modulator/transmitter 36, wiring 38 and solder (not shown).

The power component 32 can comprise an internal power source, such as a battery, or an inductive power source such as ferrite coil. A suitable ferrite coil is a small wound coil available commercially from MicroStrain, Inc. of Williston, Vt. The necessary characteristics of such a wound coil will depend to some extent on the design and selection of the other electronic components, signal source and sensor; power, frequency and size of the coil can be adjusted to suit the other components of the system. Alternatively, a suitable ferrite coil could be wound using standard equipment such as that available from Aumann North America, Inc. of Fort Wayne, Ind. The power component 32 is electrically connected to supply power to the sensor 28 (the Hall effect transducer in the first illustrated embodiment) and the other electronic components 34, 36.

Alternatively, the power component 32 could comprise an element such as a battery, for example. A lithium iodine cell available from Wilson Greatbatch Technologies, Inc. of Clarence, N.Y., could be used, for example. To conserve power, it may be desirable to employ an inductively activated switch to selectively draw power from the battery.

The sensor 28 of the first illustrated embodiment is also electrically connected to the modulator/transmitter 36 on the printed circuit board 34. The modulator/transmitter 36 serves to convert the voltage (the second signal) produced by the Hall effect transducer (sensor 28) to a transmitter signal that can be transmitted from the internal antenna to a location outside of the patient's body. For example, the modulator/transmitter 36 can encode or modulate a particular voltage (second signal) onto a radio-frequency wave (transmitter signal). This particular radio-frequency wave can then be transmitted outside of the patient's body through an internal antenna (not shown).

Suitable printed circuit boards 34 are commercially available from Advanced Circuits of Aurora, Colo. The particular layout and design of the circuit board will depend on factors such as the types of parts used for the signal source and sensor. Generally, the circuit board may be designed or laid out to minimize its size. It should be understood that the invention is not limited to any particular printed circuit board unless expressly called for in the claims. The printed circuit board 34 can be affixed to the tibial component 18 as in the embodiment of FIG. 1.

Suitable internal modulators/transmitters 36 are commercially available from Texas Instruments Inc., Dallas, Tex., in the form of electronic chips. The desired characteristics of the modulator/transmitter 36 may vary depending on other components of the system; in general, the modulator/transmitter will be of an appropriate size for implantation, will transmit at a desired frequency and will not consume excessive power. Although the illustrated embodiment utilizes a single electronic element to perform the modulation and transmission functions, these functions could be performed by separate discrete elements as well. Moreover, it should be understood that the present invention is not limited to any particular type of transmitter or transmission signal unless expressly called for in the claims.

Other possible types of data transmission include optical data transmission. An IBM personal area network may also be usable as a transmitter. Acoustic energy transmission, capacitive telemetry (using electric fields) and inductive telemetry (using magnetic fields) are also possible alternatives for transmission in the present invention.

The modulator/transmitter 36 may be attached to a hermetically sealed antenna and affixed to the tibial component 18, as in the embodiment of FIG. 1. The internal antenna may also be implanted as part of the electronics 30 of the system.

As shown schematically in FIG. 2, an external receiver 40 and data interpretation device 42 can be provided at the point of care, such as in a physician's office or at a hospital. The external receiver 40 can comprise a radio-frequency antenna that is connected to provide a signal to the data interpretation device 42. The data interpretation device 42 can be a standard computer programmed to demodulate the radio-frequency transmitter signal received from the internal transmitter 36. The data interpretation device 42 can also be a hand-held personal computer, a personal desk assistant, a laptop computer or any custom-designed data acquisition device. The data interpretation device 42 can also be programmed to perform calculations necessary to convert this particular data to a distance. It is anticipated that a software engineer or programmer could readily program the external data interpretation device 42 to calculate a distance from the particular signal received by the external antenna 40. This distance can be compared to a prior base point distance to determine if the joint space has decreased and the extent to which the joint space has decreased, to indicate the degree to which the bearing component has worn in use.

An external power source 44 can also be provided at the point of care. The external power source 44 can comprise an external coil that generates a strong localized magnetic field that is inductively coupled to the implanted ferrite coil 32 to thereby supply power to the implanted electronics 28, 34, 36. Suitable external coils are commercially available from Microstrain Inc. of Williston, Vt. Alternatively, a suitable coil could be wound using standard equipment such as that available from Aumann North America, Inc. of Fort Wayne, Ind. Generally, since the external coils are likely to be used in close proximity to the patient, it may be desirable to select or design an external coil that will not irritate or excessively heat the patient's skin and that can be easily handled by the operator or medical technician. The external coil should be able to supply a sufficient electromagnetic or magnetostatic field at the design frequency to stimulate the internal power coil.

As shown schematically in FIG. 2, the distance between the signal source 26 and the articulating surface of the femoral condyles 22 is constant, shown at $d_1$ in FIG. 2. The distance between the sensor 28 and the top surface of the proximal tibial component 18 is also constant, shown at $d_2$ in FIG. 2. The distance between the signal source 26 and the sensor 28 can vary; this distance is shown at $d_3$ in FIG. 2. It is the distance $d_3$ that is measured by the present invention. From this distance $d_3$, the thickness of the joint space 25 and thus the thickness of the bearing 16 can be calculated; the thickness of the joint space and bearing is shown at $d_4$ in FIGS. 1, 2, 4–6, 9, 11 and 15.

It may not be necessary to calculate an exact number for $d_4$. Instead, values for $d_3$ can be compared over time. Since $d_1$ and $d_2$ are constant (when the signal source and sensor are affixed to the implant components), any decrease in $d_3$ over time equals the same decrease in $d_4$ over time. Decreases in distances $d_3$ and $d_4$ correlate with wear of the bearing and changes in the joint space.

In using the first illustrated knee prosthesis system 10, the orthopaedic surgeon or medical technician would first determine a base measurement for the distance $d_3$. The patient's leg would be placed in a particular position or orientation, such as with the knee in full extension or with the patient in standing posture as shown in FIG. 1. The external power source 44 would be placed in proximity to the knee to supply power to the implanted electronics 30. When the external power source 44 is properly placed, the first signal (that is, the magnetic field or flux density) produced by the magnet (signal source 26) at its fixed location on one side of the joint space 25 or articulation 20 is received by the Hall effect transducer (sensor 28) on the opposite side of the joint space 25 or articulation 20 at its fixed location and the Hall effect transducer (sensor 28) produces and transmits an electric current or voltage (second signal) within the patient's body 31. The value of the current or voltage (second signal) produced and transmitted by the Hall effect transducer (sensor 28) depends on the magnitude of the magnetic flux density (first signal), which depends on the distance between the magnet (signal source 26) and the Hall effect transducer (sensor 28). This current or voltage is received by the modulator/transmitter 36, which then converts the value of the current or voltage (second signal) into a radio-frequency wave (transmitter signal). The transmitter signal encodes the particular voltage or current characteristic transmitted by the Hall effect transducer (sensor 28). The transmitter signal (the radio-frequency wave) is transmitted from within the patient's body by the internal modulator/transmitter 36 to the internal antenna and from the internal antenna to the external receiver 40. The external data interpretation device 42 can then determine the thickness of the joint space 25 based on the encoded data of the transmitter signal. Alternatively, the external data interpretation device 42 can calculate changes in the overall distance $d_3$ to determine whether the joint space has decreased. Changes in the thickness of the joint space 25 can thus be detected to monitor wear of the tibial bearing in the joint.

Figure 3:
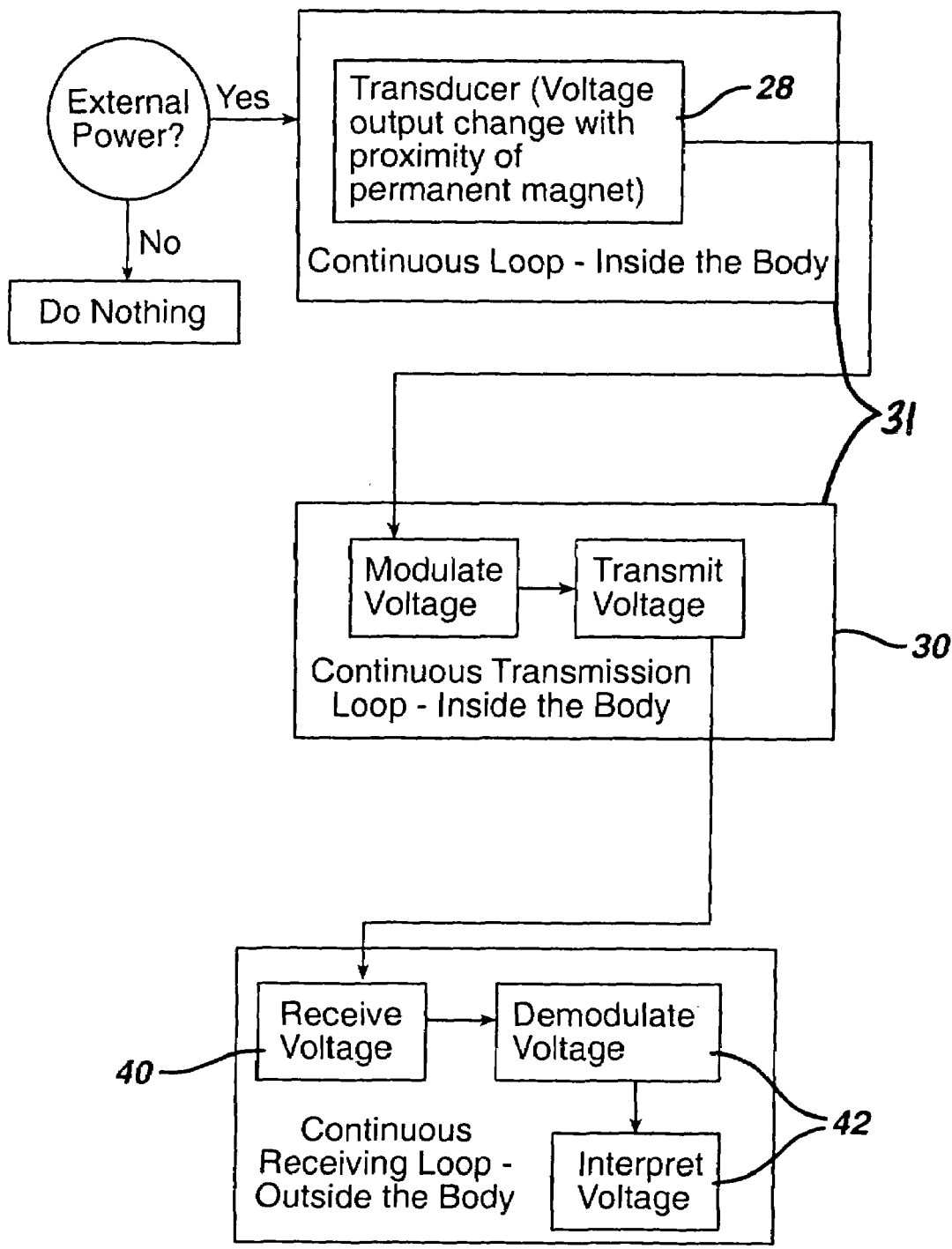
FIG. 3 is a flow chart illustrating use of the knee endoprosthesis system of FIGS. 1–2.

FIG. 3 illustrates a possible flow diagram for the first illustrated embodiment of the present invention. As there shown, if there is no external power source, the implanted electronics 28, 30 remain inactive. When an external power source is applied, the implanted power source 32 supplies electrical power to the Hall effect transducer (sensor 28). The Hall effect transducer (sensor 28) produces a voltage signal the magnitude of which corresponds with its proximity to the magnet (signal source 26) on the other side of the articulation 20. The Hall effect transducer and the magnet are in a continuous loop inside the patient's body. This voltage signal is then modulated to produce the transmitter signal that can be transmitted outside the patient's body 31 and this transmitter signal is transmitted. This process also occurs in a continuous loop within the body 31. The transmitter signal is received by the external receiver 40, and the transmitter signal is demodulated and interpreted. The process of receiving, demodulating and interpreting all takes place outside of the body 31 in a continuous loop.

Figure 4:
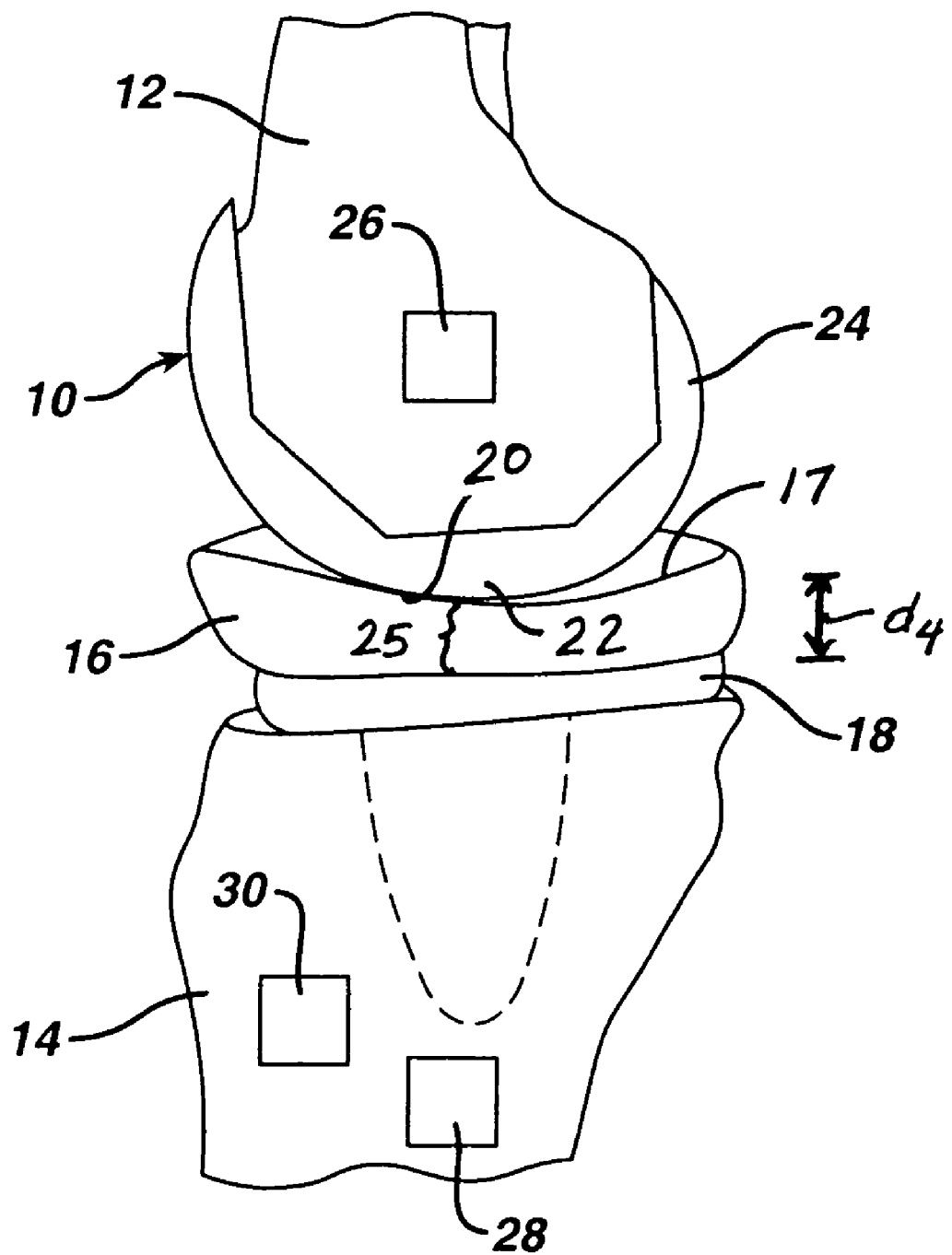
FIG. 4 is a medial/lateral elevation of a second embodiment of a knee endoprosthesis system with the distal femoral component affixed to the distal femur and the proximal tibial component affixed to the proximal tibia, showing the knee joint in extension.
Figure 5:
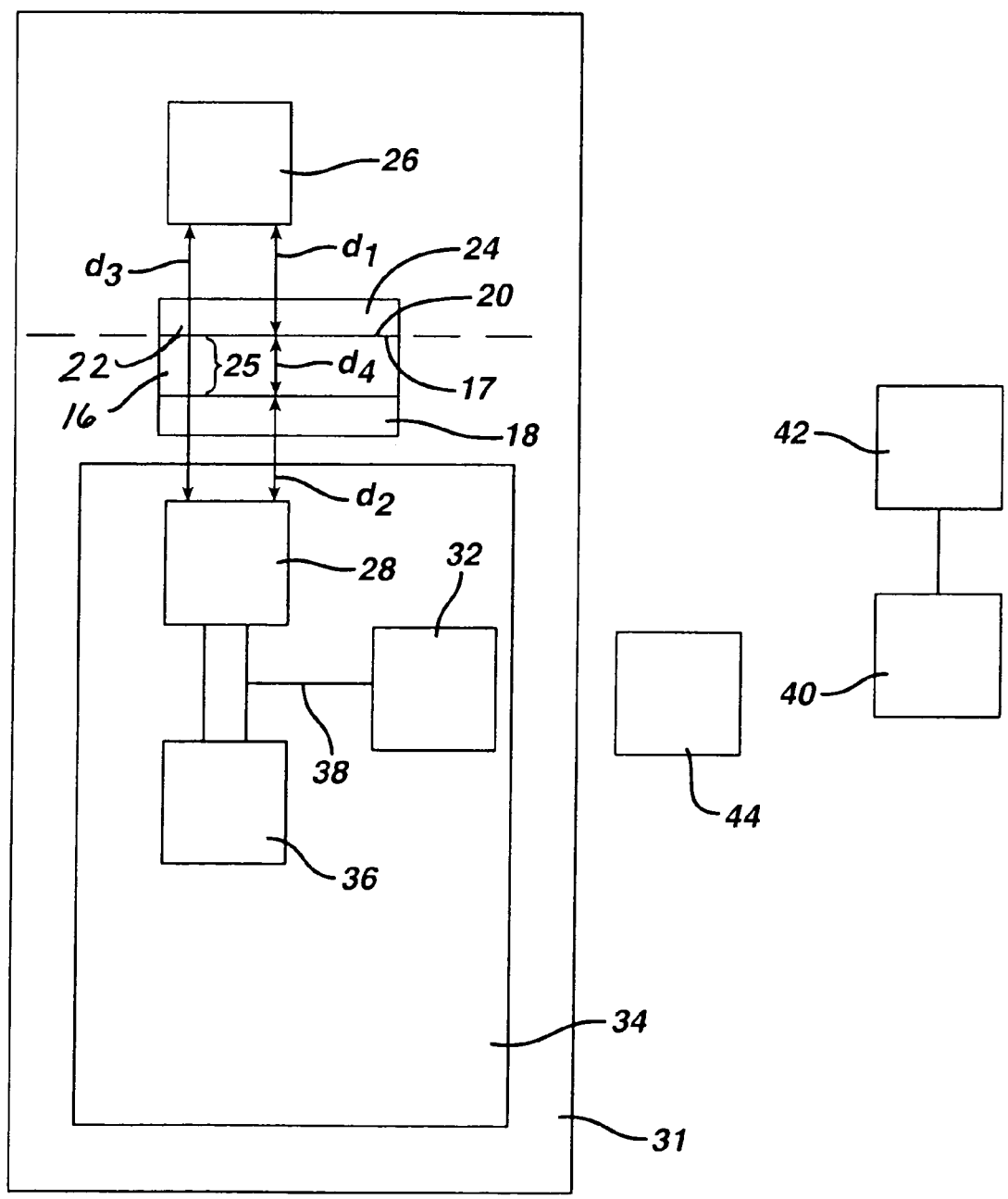
FIG. 5 is a schematic illustration of the knee endoprosthesis system of FIG. 4, showing external components of the system in addition to those implanted in the patient.

Variations in the first illustrated embodiment are possible. For example, the endoprosthesis system can be provided in the form of a kit with one or more of the electronic and signal generating components provided as a discrete element. For example, the electronic components 30 and sensor 28 could be supplied as one or more separate discrete packages to be affixed to the patient's bones instead of to the components of the implant itself. Alternatively, the signal source 26 could be supplied as a separate discrete component to be affixed to the patient's bone. Moreover, all of the electronic components 30, sensor 28 and the signal source 26 could be supplied as separate discrete components to be affixed to the patient's bones. FIGS. 4–5 illustrate a knee endoprosthesis system similar to that of the embodiment illustrated in FIGS. 1–2, except with the signal source 26, sensor 28 and other electronics 30 all affixed to the femur 12 and the tibia 14, spaced from the implant components 16, 18, 24. Bone cement or other means, such as an adhesive, could be used to affix these components 26, 28, 30 to the patient's femur 12 and tibia 14.

In addition, it may be desirable to provide a plurality of sensors as part of a kit or endoprosthesis system. A plurality of sensors could be used to provide for redundancy in case of failure of one or more of the sensors, or could be used to measure distances in different parts of the joint, such as in the medial and lateral portions of the tibial bearing. Three-dimensional sensing may also be employed to improve accuracy and to compensate for potential migration or subsidence of bone-affixed implants.

Figure 6:
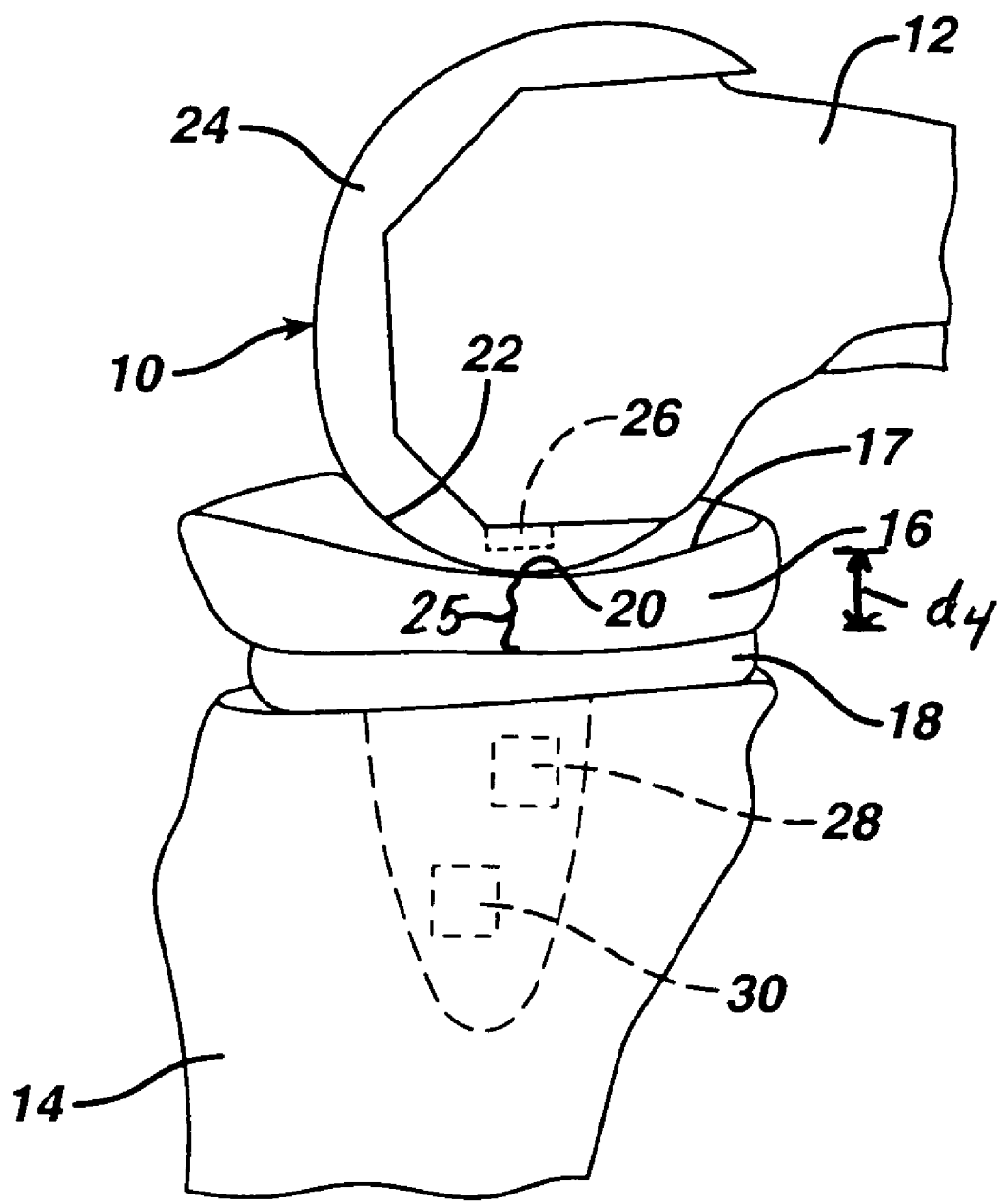
FIG. 6 is a medial/lateral elevation of an embodiment of a knee endoprosthesis system with the distal femoral component affixed to the distal femur and the proximal tibial component affixed to the proximal tibia, showing the knee joint in flexion.
Figure 7:
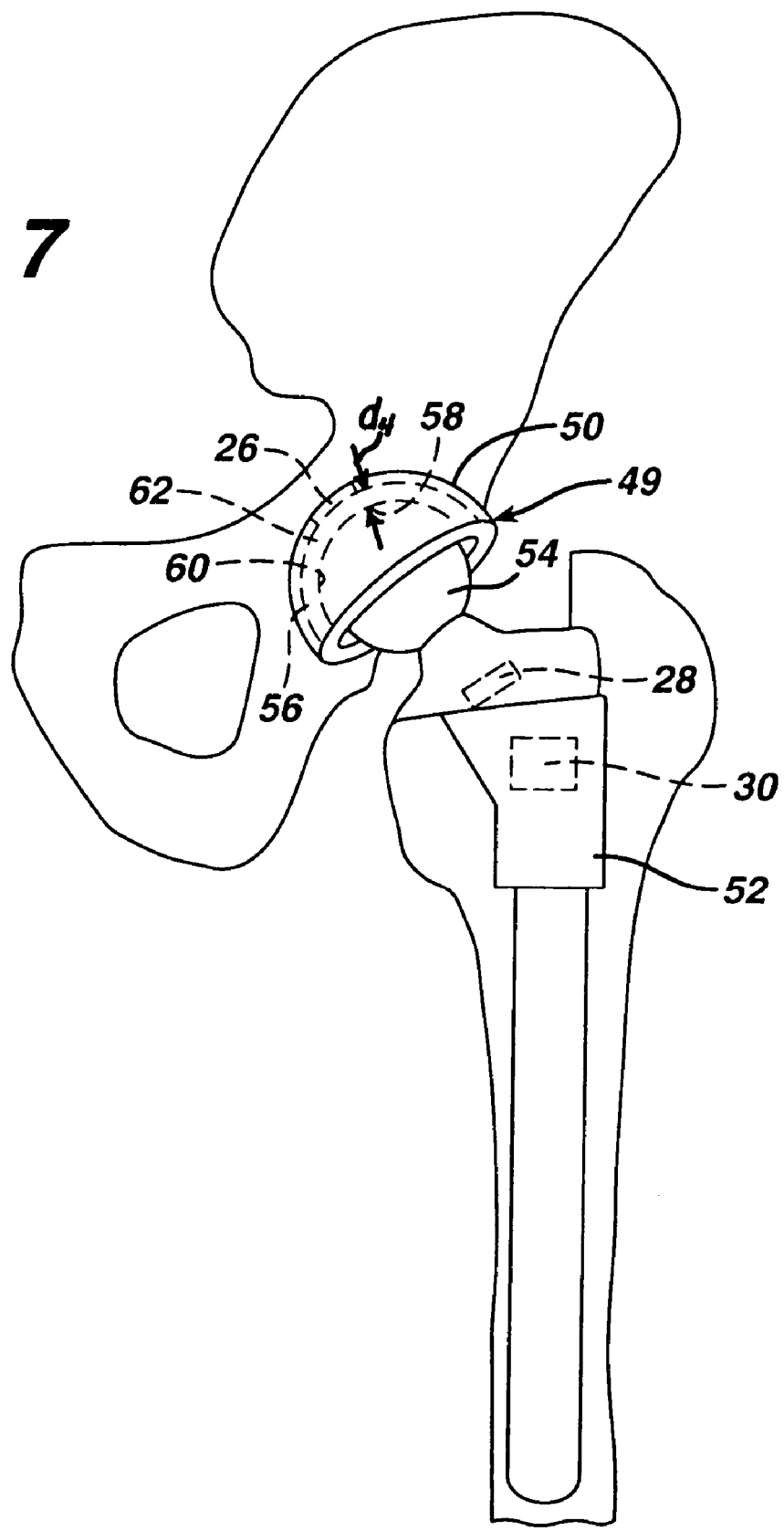
FIG. 7 is an anterior elevation of an embodiment of a hip endoprosthesis system with the acetabular cup affixed to the hip bone and the proximal femoral component affixed to the proximal femur.

Although the first two illustrated embodiments show the knee in extension, the system of the present invention could also be used to evaluate the condition of the tibial bearing 16 with the knee in flexion as shown in FIG. 6. For evaluation with the knee in flexion, the positions or alignment of the signal source 26 and sensor 28 may be adjusted for optimization of transmission of the first signal.

A third embodiment of a prototype knee endoprosthesis system is illustrated in FIG. 15. As in the embodiments of FIGS. 1, 8 and 10, the prototype knee endoprosthesis system of the embodiment of FIG. 15 includes a distal femoral component 24A, proximal tibial component 18A and bearing component 16A, although in this embodiment, the proximal tibial component 18A and bearing component 16A have some different features, as described in more detail below.

Figure 8:
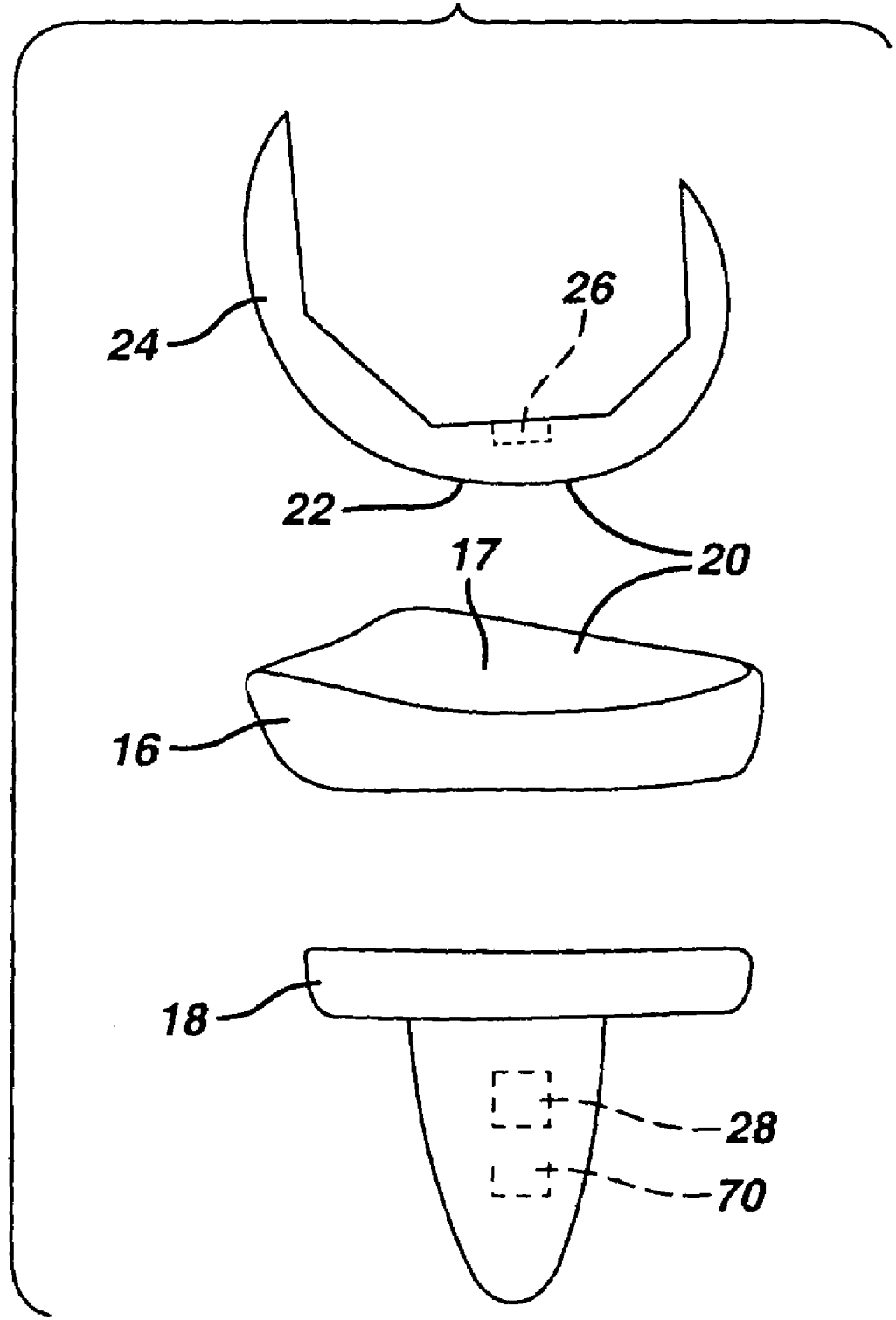
FIG. 8 is an elevation of the components of an embodiment of a knee endoprosthesis system shown prior to implantation.

As in the embodiments of FIGS. 1 and 8, in the embodiment of FIG. 15 the distance reference 28 comprises a Hall effect transducer and the signal source 26 comprises a magnet. The Hall effect transducer (distance reference 28) in the embodiment of FIGS. 15 and 16 is carried on a circuit board 34 on the proximal surface 29 of the tibial tray 18A, and fits within a recess 33 in the distal surface of the tibial bearing 16A, although it should be understood that this embodiment is a prototype and that in a final embodiment these components could be carried elsewhere in the tibial component. The signal source 26 is a magnet is carried by the femoral component 24A.

Figure 18:
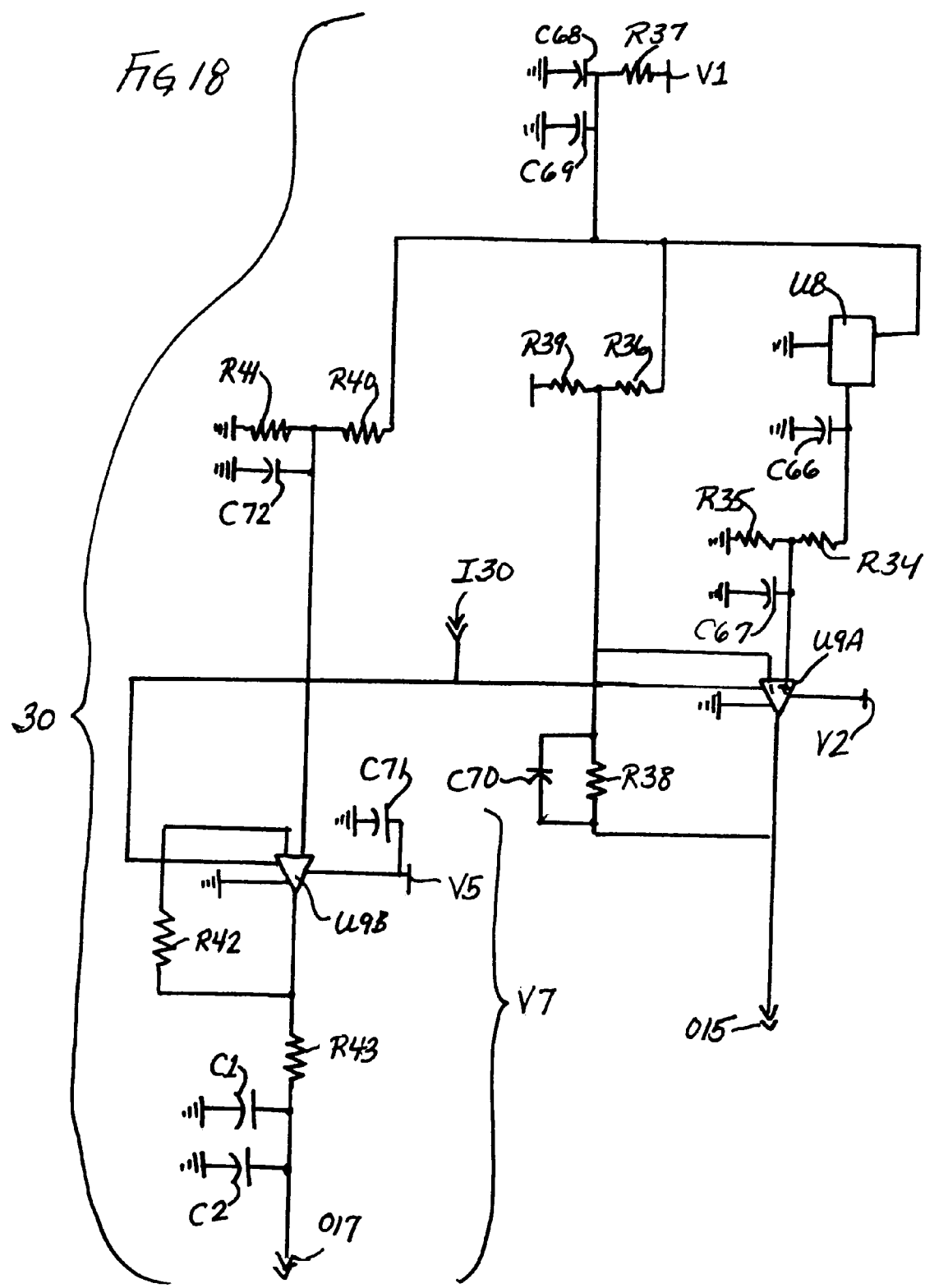
FIG. 18 is a schematic of electronics associated with the Hall effect sensor.
Figure 19:
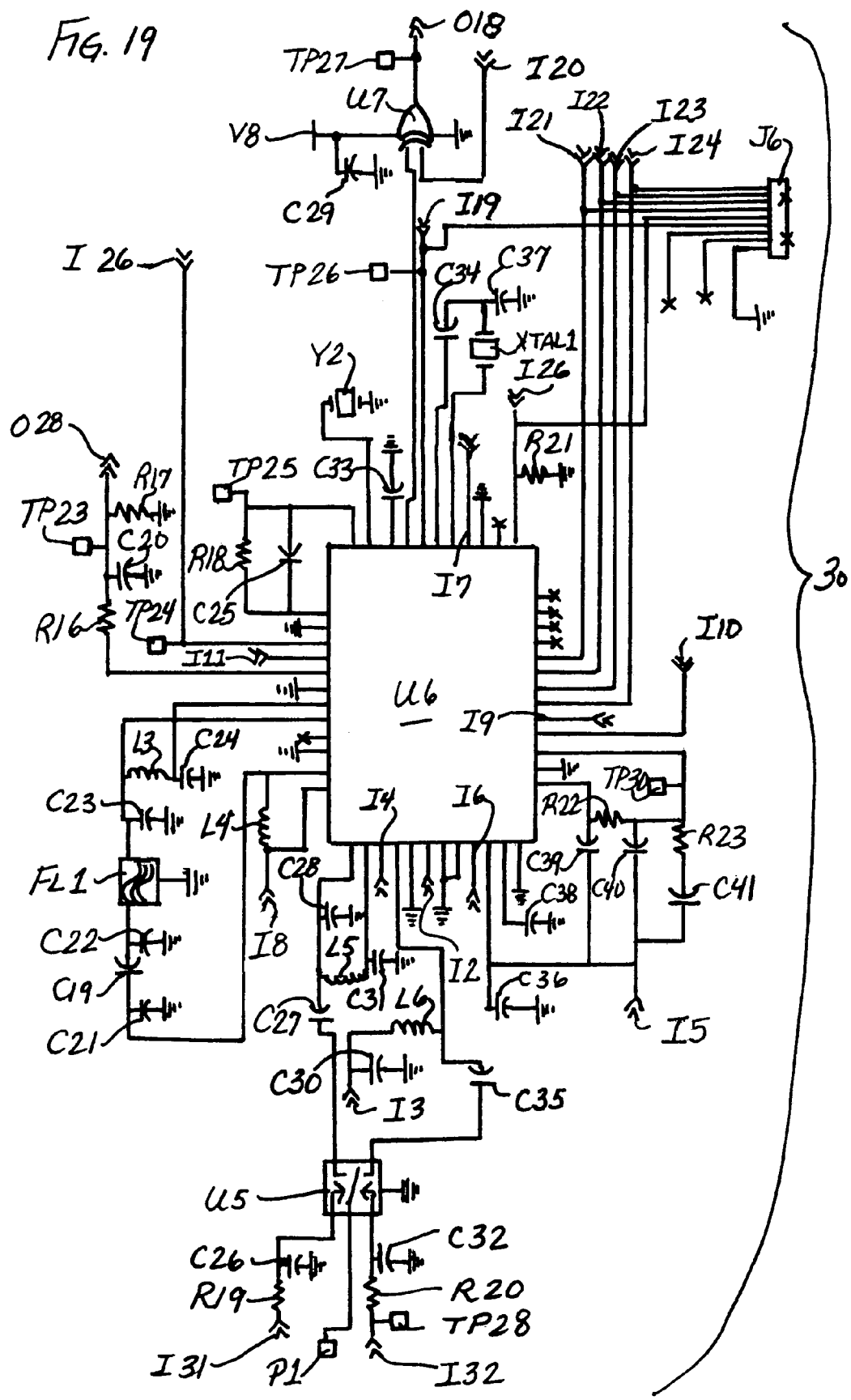
FIGS. 19 and 19A are schematics of a 900 MHz RF transceiver circuit.
Figure 19A:
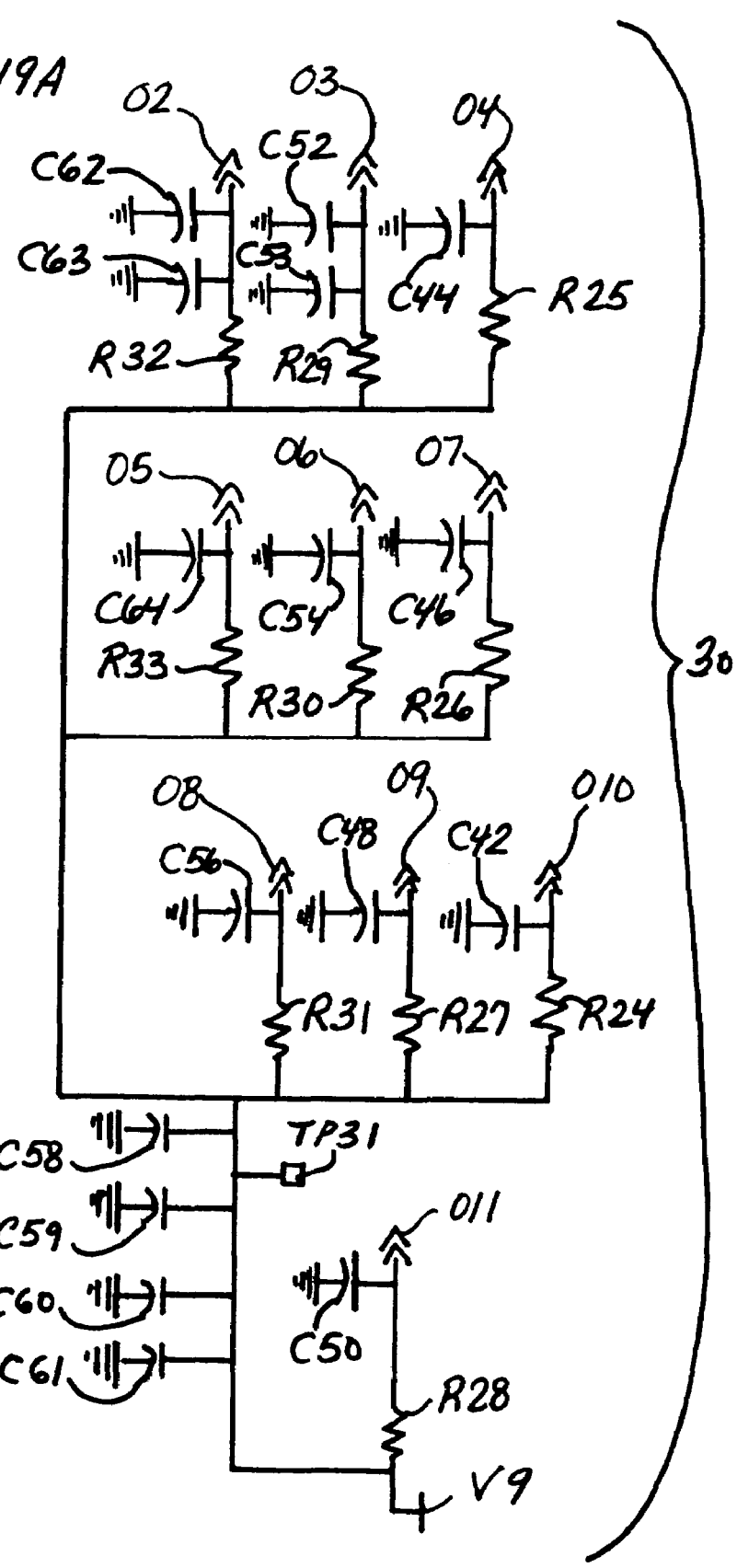
Figure 20:
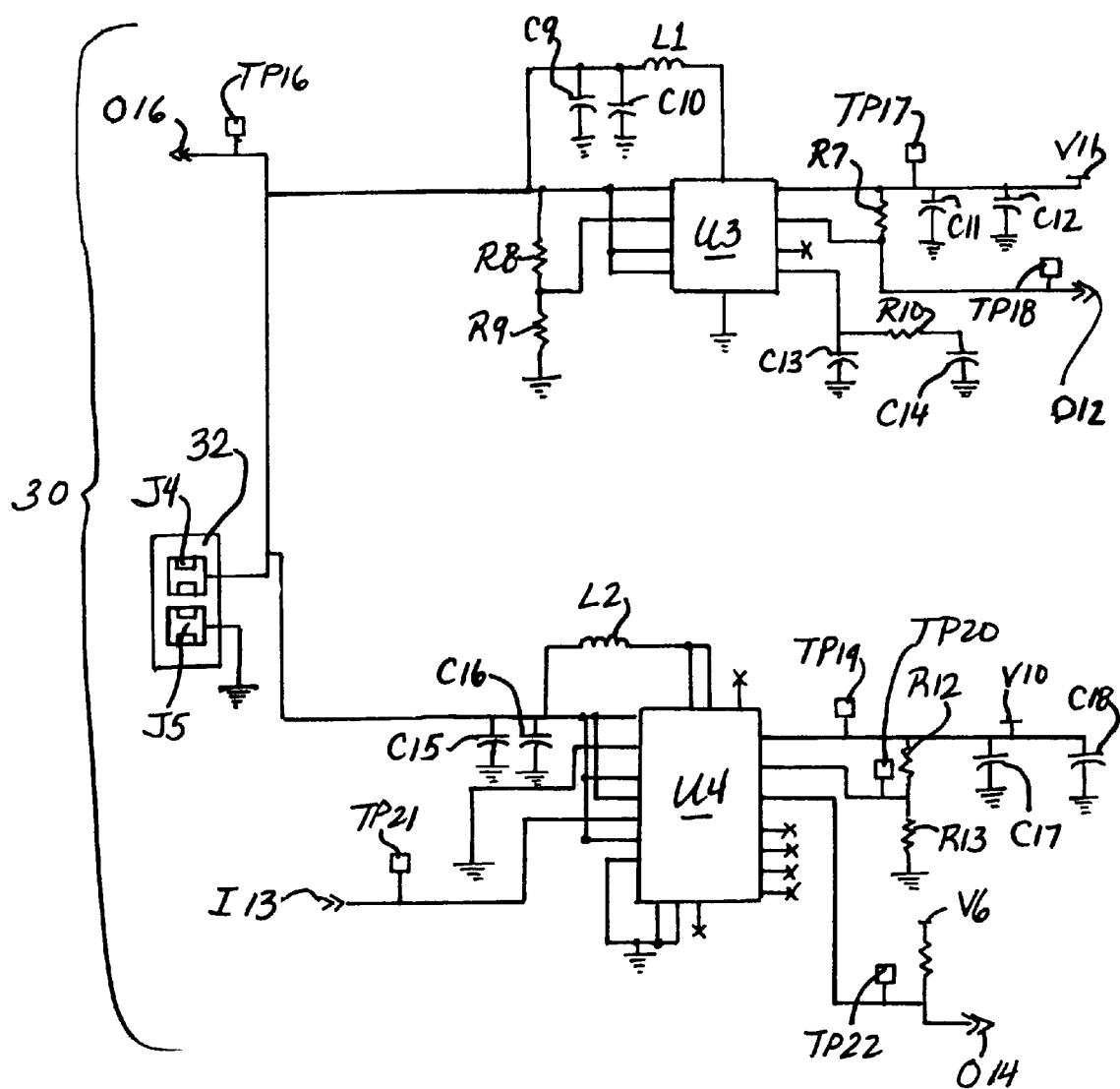
FIG. 20 is a schematic of power regulation circuitry to provide 2.8 volt and 5 volt fixed inputs.
Figure 21:
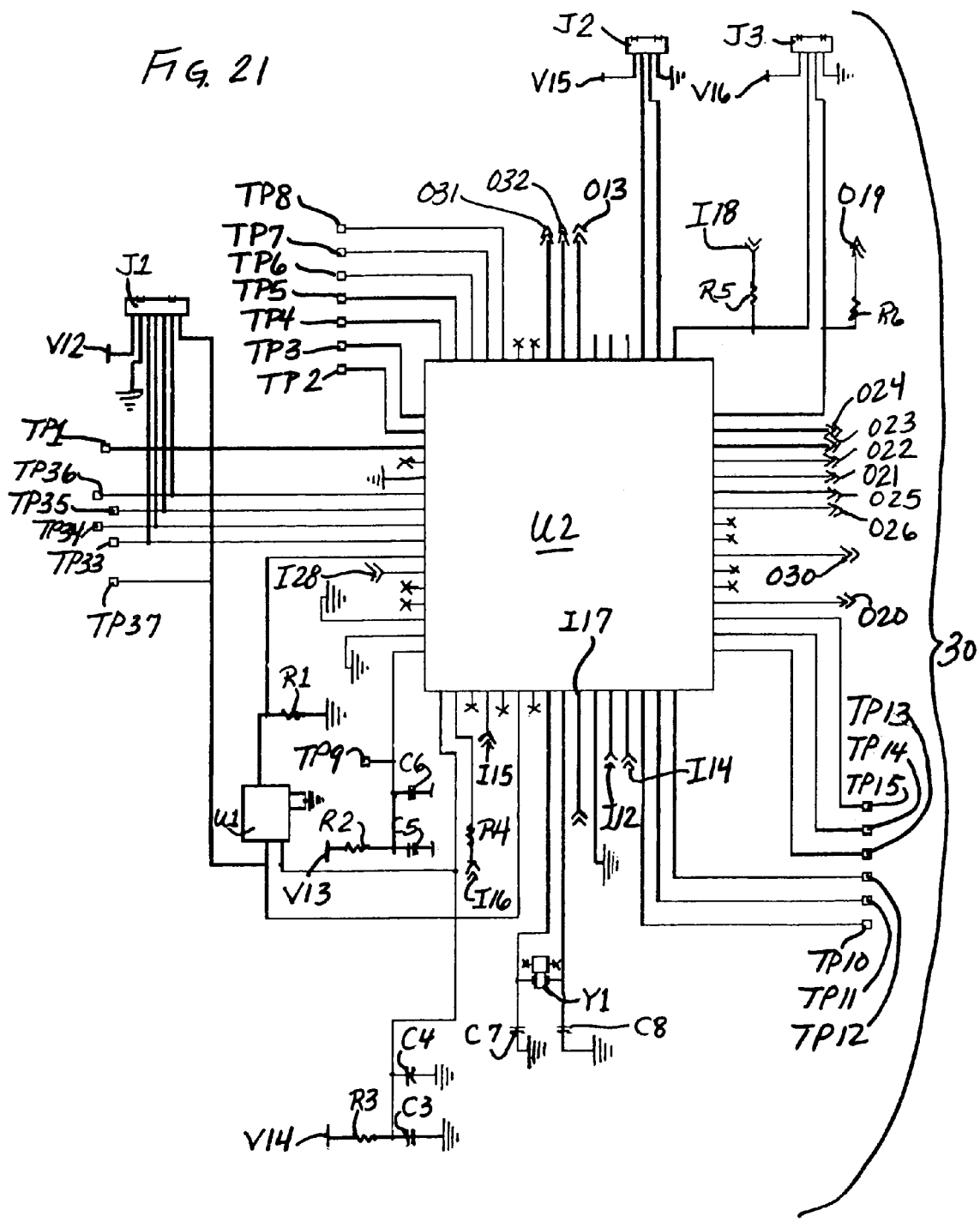
FIG. 21 is a schematic of a microcontroller circuit.
Figure 22:
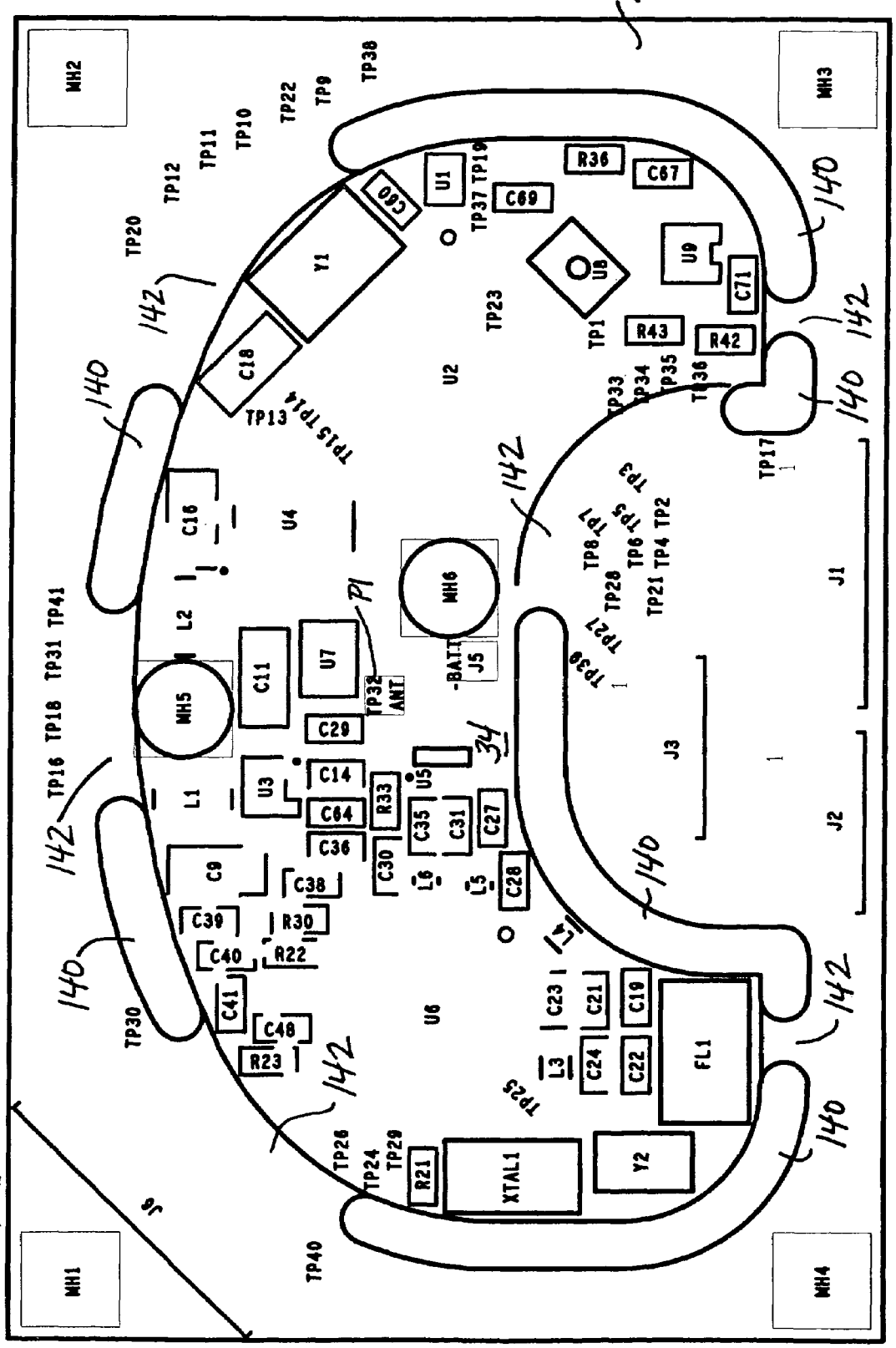
FIG. 22 is a silk-screen layout of the top layer of a printed circuit board on which the components of FIGS. 18–21 are mounted.
Figure 23:
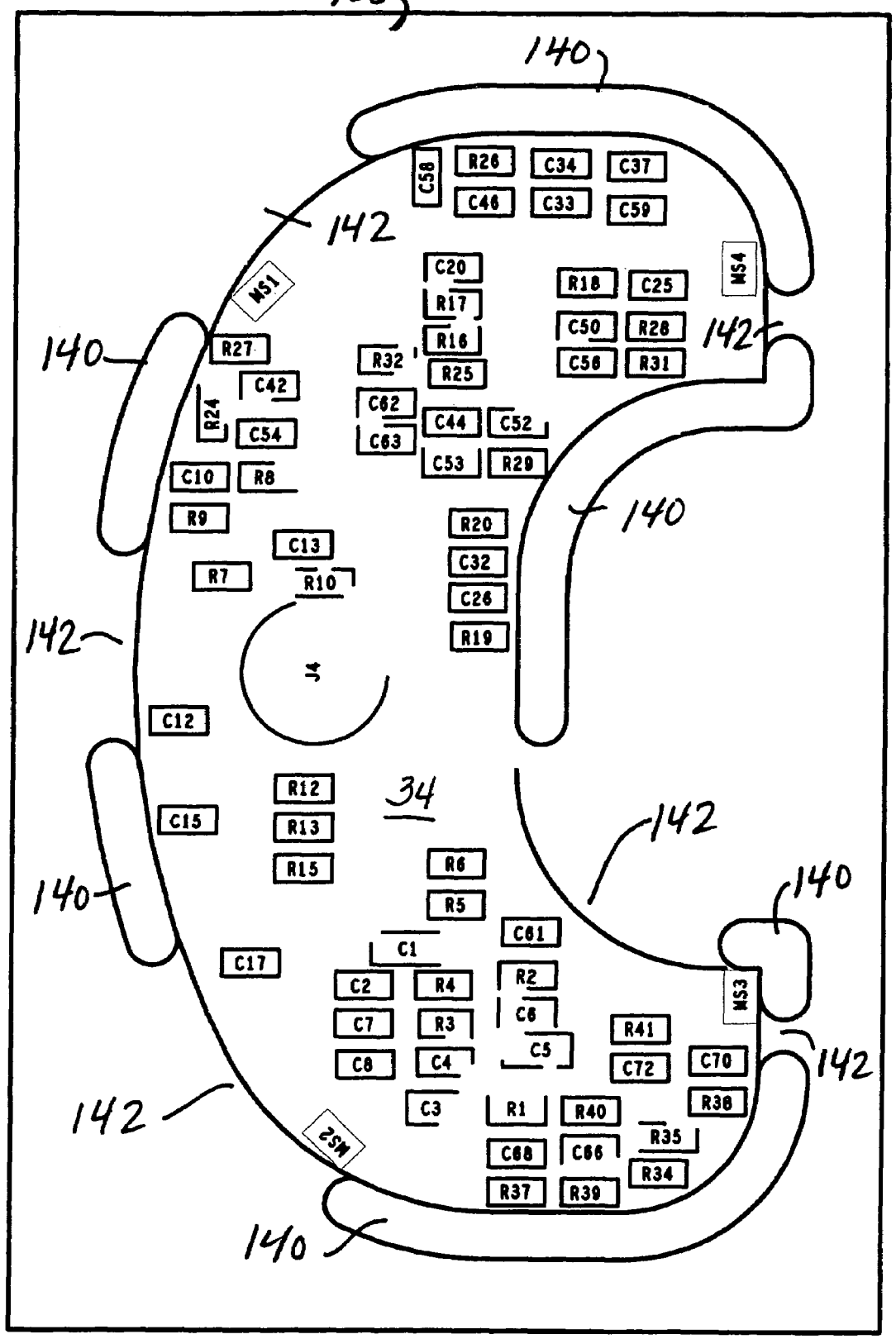
FIG. 23 is a silk-screen layout of the bottom layer of the printed circuit board of FIG. 22.

Examples of schematics for the Hall effect transducer 28 circuit, transceiver circuit, power regulation circuit and control component circuit of the embodiment of FIGS. 15–16 are illustrated in FIGS. 18–21. FIG. 18 illustrates a schematic for the circuit associated with the Hall effect transducer 28 circuit. FIGS. 19 and 19A illustrate a schematic for a 900 MHz RF transceiver circuit. FIG. 20 illustrates a schematic of power regulation circuitry to provide 2.8 volt and 5 volt fixed inputs. FIG. 21 illustrates a schematic of a microcontroller circuit. All of these circuits are carried by the circuit board shown at 34 in FIGS. 15 and 16. The silk-screen layout for the multi-layered circuit board 34 is shown in FIGS. 22–23.

The resistors shown in FIGS. 18–21 are described in the following table:

| FIGS. 18–21 RESISTORS | | | |
|---|---|---|---|
| Reference | Value (Ohm) | Manufacturer | Manufacturer Part Number |
| R1, R15, R21, R38, R42 | 100 K | Panasonic | ERJ-2RKF1003X |
| R2, R3 | 10 | Panasonic | ERJ-2RKF10R0X |
| R4 | 26.7 K | Panasonic | ERJ-2RKF2672X |
| R5, R6 | 0 | Panasonic | ERJ-2GE0R00X |
| R7 | 511 K | Panasonic | ERJ-2RKF5113X |
| R8, R9 | 499 K | Panasonic | ERJ-2RKF4993X |
| R12, R36, R39 | 1 M | Panasonic | ERJ-2RKF1004X |
| R13 | 110 k | Panasonic | ERJ-2RKF1103X |
| R16 | 4.99 K | Panasonic | ERJ-2RKF4991X |
| R17 | 66.5 k | Panasonic | ERJ-2RKF6652X |
| R18 | 220 K | YAGEO AMERICA | 9C04021A2203FLHF3 |
| R20, R19 | 100 | Panasonic | ERJ-2RKF1000X |
| R22 | 26.7 K | Panasonic | ERJ-2RKF2672X |
| R23 | 12.1 K | Panasonic | ERJ-2RKF1212X |
| R24, R25, R26, R27, R28, R29, R30, R31, R32, R33, R37, R43 | 10 | Panasonic | ERJ-2RKF10R0X |
| R34, R35, R40, R41 | 200 K | Panasonic | ERJ-2RKF2003X |

The capacitors shown in the circuits of FIGS. 18–21 are described in the following table:

| FIGS. 18–21 CAPACITORS | | | |
|---|---|---|---|
| Reference | Value | Manufacturer | Manufacturer Part Number |
| C1, C3, C5 | 4.7 uF | Panasonic | ECJ-1VB0J475M |
| C2, C10, C12, C15, C17, C26, C29, C32, C42, C44, C46, C48, C50, C52, C54, C56, C58, C59, C60, C61 C62, C64, C68, C71, | 0.1 uF | Kemet | C0402C104K8PACTU |
| C4, C6, C14 | 0.01 uF | Kemet | C0402C103J3RACTU |
| C7, C8, C13 | 10 pF | Panasonic | ECJ-0EC1H100D |
| C9, C11, C16, C18 | 22 uF | Panasonic | ECJ-3YF1A226Z |
| C19, C22 | 82 pF | Panasonic | ECJ-0EC1H820J |
| C20 | 47000 pF | Panasonic | ECJ-0EB1A473K |
| C21, C37 | 15 pF | YAGEO AMERICA | 0402CG150J9B200 |
| C23 | 120 pF | Panasonic | ECJ-0EC1H121J |
| C24 | 68 pF | Panasonic | ECJ-0EC1H680J |
| C27, C25 | 22 pF | Panasonic | ECJ-0EC1H220J |
| C31, C28 | 2.7 pF | BC Components | 0402N2R7C500NT |
| C30 | 150 pF | YAGEO AMERICA | 0402CG151J9B200 |
| C41 | 1500 pF | Panasonic | ECJ-0EB1E152K |
| C33 | 1500 pF | Panasonic | ECJ-0EB1E152K |
| C34 | 18 pF | Panasonic | ECJ-0EC1H180J |
| C35 | 1.8 pF | BC Components | 0402N1R8C500NT |
| C36, C53, C63, C69 | 10000 pF | BC Components | 0402C103K4RACTU |
| C38, C40, C66, C67, C70, C72 | 100 pF | BC Components | 0402N101J500NT |
| C39 | 47 pF | Panasonic | ECJ-0EC1H470J |

Other components shown in the circuits of FIGS. 18–21 are described in the following table:

| FIGS. 18–21 Other Components and References | | | | |
|---|---|---|---|---|
| Reference | Description | Value | Manufacturer | Manufacturer Part Number |
| FL1 | Ceramic Chip Filter | $f_c = 10.7$ MHz | Murata | SFECV10M7HA00-R0 |
| J1 | Through-Hole Connector | B 7B-ZR-SM3-TF | JST | B 7B-ZR-SM3-TF |
| J2, J3 | Serial Debug Port and RF Serial Debug Port | B 4B-ZR-SM3-TF | JST | B 4B-ZR-SM3-TF |
| J4 | Alkaline Battery | BatteryPlus | | PADS on PCB |
| J5 | Alkaline Battery | BatteryNeg | | PADS on PCB |
| J6 | RF Debug Programming Port | B 9B-ZR-SM3-TF | JST | B 9B-ZR-SM3-TF |
| L1 | Inductor | 10 uH | Coilcraft | D03314-103M |
| L2 | Inductor | 33 uH | Coilcraft | D03314-333M |
| L3 | Inductor | 4.7 uH | Murata | LQG21CR47N00 |
| L4 | Inductor | 4.7 uH | Murata | LQG21CR47N00 |
| L5 | Inductor | 10 nH | Murata | LQW18AN10NG00D |

FIGS. 18–21 Other Components and References -continued

| Reference | Description | Value | Manufacturer | Manufacturer Part Number |
|---|---|---|---|---|
| L6 | Inductor | 8.2 nH | Murata | LQW18AN8N2D00D |
| MH1–MH4 | Outer Mounting Holes | MountingHole120 | | |
| MH5–MH6 | Inner Mounting Holes | MountingHole94 | | |
| MS1–MS4 | | Standoff_smd | Components Corp. | TP-108 (Mounted on SIDE) |
| TP1–TP41 | Test Points | | PADS on PCB | TP1–TP41 |
| U1 | Ultrasmall Supply Voltage Supervisor | | Texas Instruments | TPS3800G27 DCKR | U1 |
| U2 | 16 bit ultralow power microcontroller | | Texas Instruments | MSP430F149 IPM | U2 |
| U3 | low input voltage synchronous boost converter with fixed 2.8 volt output | | Texas Instruments | TPS61014DGS | U3 |
| U4 | adjustable 95% efficient boost converter with 120 mA LDO | | Texas Instruments | TPS61100PW | U4 |
| U5 | GaAs MMIC (transmit receive switch) | | Hittite | HMC226 | U5 |
| U6 | Single chip RF transceiver | | Texas Instruments | TRF6901PT | U6 |
| U7 | XOR | | Texas Instruments | SN74LVC1G86DBVR | U7 |
| U8 | Linear ratiometric Hall effect sensor | | Allegro Micro | | U8 |
| U9 | Operational Amplifier | | Texas Instruments | OPA2363IDGST | U9 |
| XTAL1 | Crystal oscillator (19.6608 MHz) | | Citizen | CS10-19.6608MABJTR | XTAL1 |
| Y1 | Crystal oscillator (32768 Hz) | | Citizen | CM155-32.768KDZFTR | Y1 |
| Y2 | 10.7 MHz oscillating Discriminator | | Murata | CDSCB10M7GA119-R0 | Y2 |
| P1 | Pad for Antenna Wire | | | | |

It should be understood that the circuits of FIGS. 18–21 are interconnected in the illustrated embodiment. The following table identifies the interconnections, using the prefixes "O" and "I" to indicate where the interconnections are located:

| Reference | | |
|---|---|---|
| Out | In | Description |
| O2 (FIG. 19A)/ | I2 (FIG. 19) | PA VCC1 |
| O3 (FIG. 19A) | I3 (FIG. 19) | PA VCC2 |
| O4 (FIG. 19A) | I4 (FIG. 19) | LNA VCC |
| O5 (FIG. 19A) | I5 (FIG. 19) | VCO VCC2 |
| O6 (FIG. 19A) | I6 (FIG. 19) | VCO VCC1 |
| O7 (FIG. 19A) | I7 (FIG. 19) | XTAL VCC |
| O8 (FIG. 19A) | I8 (FIG. 19) | MIX VCC |
| O9 (FIG. 19A) | I9 (FIG. 19) | DVDD |
| O10 (FIG. 19A) | I10 (FIG. 19) | CP VCC |
| O11 (FIG. 19A) | I11 (FIG. 19) | DEM VCC |
| O12 (FIG. 20) | I12 (FIG. 21) | LOW BATT 3 V |

-continued

| Reference | | |
|---|---|---|
| Out | In | Description |
| | | Triggers LOW when VBAT < 1 V |
| O13 (FIG. 21) | I13 (FIG. 20) | 5 V ENABLE |
| O14 (FIG. 20) | I14 (FIG. 21) | 5 V POWER GOOD |
| O15 (FIG. 18) | I15 (FIG. 21) | Sensor Voltage |
| O16 (FIG. 20) | I16 (FIG. 21) | V BATT |
| O17 (FIG. 18) | I17 (FIG. 21) | Reference Voltage |
| O18 (FIG. 19) | I18 (FIG. 21) | RF RX Data |
| O19 (FIG. 21) | I19 (FIG. 19) | RF TX Data |
| O20 (FIG. 21) | I20 (FIG. 19) | FR FX LOSIDE |
| O21 (FIG. 21) | I21 (FIG. 19) | RF MODE |
| O22 (FIG. 21) | I22 (FIG. 19) | RF Data |
| O23 (FIG. 21) | I23 (FIG. 19) | RF Strobe |
| O24 (FIG. 21) | I24 (FIG. 19) | RF Clock |
| O25 (FIG. 21) | I25 (FIG. 19) | RF LRN Hold |
| O26 (FIG. 21) | I26 (FIG. 19) | RF Stdby |
| O28 (FIG. 19) | I28 (FIG. 21) | RF RSSI |
| O30 (FIG. 21) | I30 (FIG. 18) | 5 V MEASURE ENABLE |

-continued

| | Reference | |
|---|---|---|
| Out | In | Description |
| O31 (FIG. 21) | I31 (FIG. 19) | rf ant rx |
| O32 (FIG. 21) | I32 (FIG. 19) | |

Voltage references for the circuits of FIGS. 18–21 are set forth in the following table:

| Voltage References | |
|---|---|
| Reference | Description |
| V1 (FIG. 18) | +5 Volts |
| V2 (FIG. 18) | +2.8 Volts |
| V5, V6 (FIG. 18) | +2.8 Volts |
| V7 (FIG. 18) | 2.5 Volt Ratiometric Reference |
| V8 (FIG. 19) | +2.5 Volts |
| V9 (FIG. 19A) | +2.8 Volts |
| V10 (FIG. 20) | +5 Volts |
| V11 (FIG. 20) | +2.8 V |
| V12, V13, V14, V15, V16 | +2.8 V |

Referring again to FIGS. 15–16, the power source in this embodiment comprises a standard AAAA alkaline battery shown at 32 in FIGS. 15–16 and FIG. 20. It should be understood that other types of batteries could be used, preferably batteries that have extended useful lives and that are biocompatible and small. The battery 32 in this embodiment is held by a support member 106 and is electrically connected to the circuits of the circuit board 34 through electrical leads 108. 110. The circuits of the circuit board 34 are also electrically connected to an RF antenna wire 112 at the pad P1 (see FIGS. 19 and 22).

As shown in FIGS. 15–17, the support member 106 has a substantially tubular body 114 open at its proximal end 116, a threaded distal end portion 118 and an intermediate threaded portion 120 between the tubular body 114 and the threaded distal end portion 118.

The tubular body 114 has an open interior sized and shaped to hold a substantial part of the length of the internal power source 32, and an exterior sized and shaped to fit within the hollow stem 122 of the tibial component 18A. The tubular body 114 also has a pair of diametrically-opposed longitudinal slots, one of which is shown at 124 in FIG. 17 and the other shown at 125 in FIG. 17A. Each longitudinal slot 124, 125 extends from the proximal end 116 of the tubular body 114 along a portion of the length of the body 114 toward the distal end. As can be seen from a comparison of FIGS. 17 and 17A, one of the slots 124 extends to and connects with the intermediate threaded portion 120 and the other slot 125 extends to a point spaced from the intermediate threaded portion 120. Each longitudinal slot is connected to a mounting slot 126, 128. Each mounting slot 126, 128 extends around a small portion of the circumference of the tubular body 114 perpendicular to the longitudinal slots and includes an enlarged portion extending in the proximal direction. The longitudinal slots 124, 125 and mounting slots 126, 128 cooperate with a pair of diametrically opposed mounting lugs 130, 132 (see FIG. 15) on the interior wall of the tibial stem 122 to secure the support member in position inside the tibial stem 122. A coil spring (not shown) within the tubular body 114 biases the battery in the proximal direction.

In addition to supporting and positioning the internal power source within the tibial stem, the support member 106 also serves to position and support the RF antenna wire 112. The RF antenna wire 112 extends from the antenna mounting pad P1 on the circuit board 34 distally down through the hollow tibial stem 122. The antenna wire 112 extends through the longer longitudinal slot 124 to the intermediate threaded portion 120 of the support member 106, and then is wound around the threads of the intermediate threaded portion 120, as illustrated in FIG. 15. An end cap 136 is threaded onto the threaded distal end 118 of the support member. The end cap 136 has a tubular portion that surrounds at least part of the intermediate threaded portion 120 and the distal part of the antennae wire 112. Both the end cap 136 and the support member 106 may be made of a suitable biocompatible plastic material, such as ultrahigh molecular weight polyethylene for example.

Referring now to FIGS. 22 and 23, these drawings illustrate the silk-screen layout of the circuit board 34 during the manufacturing process. The overall rectangular board illustrated at 138 is a transitional structure, used at the time of programming the components of the circuit board 34, but which is cut to fit within the tibial tray after programming. Accordingly, some of the components of the circuits of FIGS. 18–21 are located at the periphery of the transitional board 138; these peripheral components are not needed when the circuit board 34 is assembled with the tibial component and implanted. The circuit components of FIGS. 18–21 that are to be implanted used during operation of the joint space measurement device are positioned within the outline of the portion of the board that will be implanted. For ease of manufacture, the transitional board 138 has a plurality of spaced cut-outs 140 positioned at the outline of the portion to be implanted; the cut-outs are connected by bridging sections 142 that can be readily cut to shape the final circuit board that will be implanted.

To program the programmable components of the circuits illustrated in FIGS. 18–21, programming tools may be used such as those available from IAR Systems Software, Inc. of Foster, Calif. and Marlborough, Mass. For analysis and display of RF data transmitted by the implant, hardware and software may be used such as LabView software and associated equipment available from National Instruments Corporation of Austin, Tex.

The Hall effect transducer or sensor of the embodiment of FIGS. 15–21 has a resolution of about 0.001 mm (1 micron). The overall system of this embodiment has a resolution of about 0.1 mm (100 microns). It should be understood that the embodiment of FIGS. 15–21 is a prototype; greater sensitivity of the overall system can be achieved with the use of precision electrical components, optimized software and redundancy of multi-dimensional sensors using multiple signal sources. In addition, it is anticipated that a system developed from this prototype would use a different power source and would use miniaturized electronics.

Although the signal source 26 is shown associated with the distal femur in the above-described knee endoprostheses, the invention is not limited to such an arrangement unless expressly called for in the claims. For example, the signal source could be associated with the proximal tibia and the sensor could be associated with the distal femur. Or, as shown in the embodiment of FIGS. 24–25, two implanted signal sources could be used, one signal source associated with the implant or bone on one side of the joint space and the other signal source associated with the implant or bone on the opposite side of the joint space, with the sensor being located outside of the patient's body.

Figure 24:
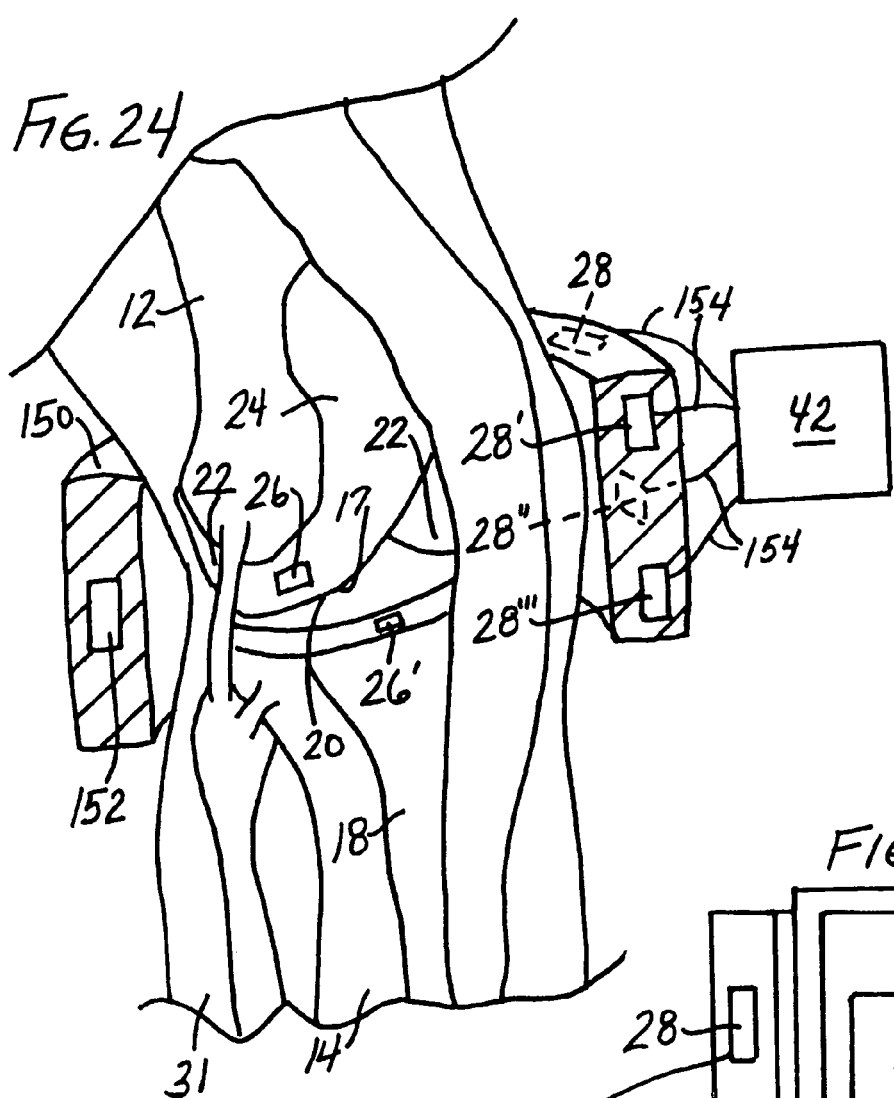
FIG. 24 is a perspective view of another embodiment of a knee endoprosthesis system with the distal femoral component affixed to the distal femur and the proximal tibial component affixed to the proximal tibia, shown with surrounding tissue in outline and shown with an external cuff (in cross-section) around the knee.
Figure 25:
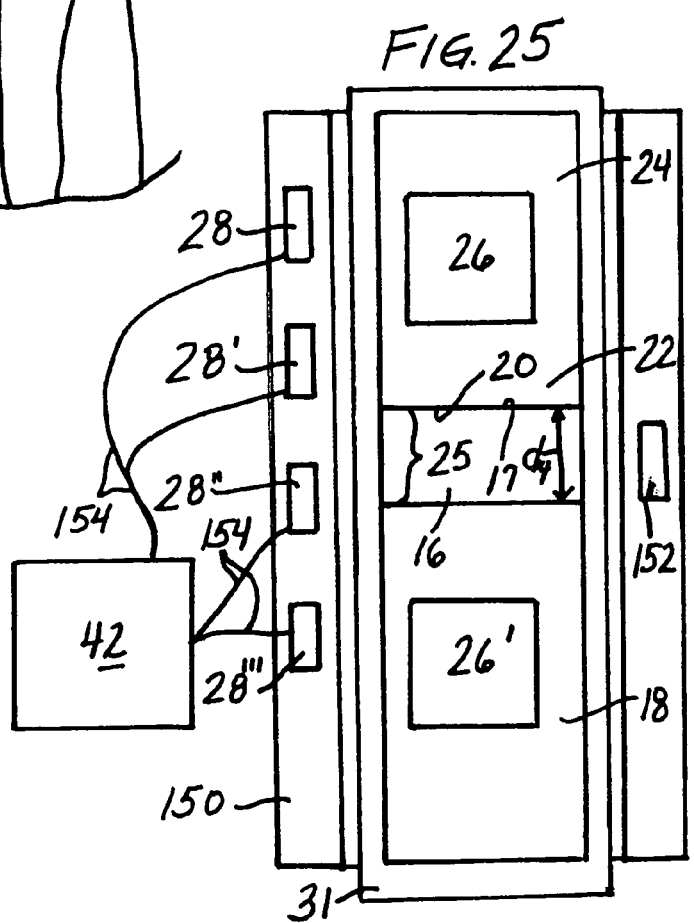
FIG. 25 is a schematic illustration of the knee endoprosthesis system of FIG. 24, showing external components of the system in addition to those implanted in the patient.

In the embodiment of FIGS. 24–25, each signal source 26, 26' comprises a superparamagnet affixed to one of the implant components. Multiple sensors 28, 28', 28", 28"', such as Hall effect transducers, are located within an external cuff 150 that can be placed around the affected joint. The cuff 150 can also carry a field source 152 that serves to selectively magnetize the signal sources. For example, the superparamagnet 26 in the femoral component 24 could be selected to produce a specific magnetic field perturbation when subjected to a particular magnetic field and the superparamagnet 26' in the tibial component 18 could be selected to product a different magnetic field perturbation when subjected to a particular magnetic field. In use, the cuff 150 would be maintained in a constant position throughout the process; for this purpose, the cuff may, for example, be inflatable to secure it in position throughout the measurement. Both superparamagnets 26, 26' would then be magnetized and the perturbation in the magnetic field sensed; a suitable algorithm could be used to determine a distance corresponding with this perturbation in the magnetic field. The magnetic field source 152 (or sources if a plurality of magnetic field sources are used) in the cuff 150 could produce a pulsed magnetic signal and the magnetic field resulting from the interaction of each pulse and the superparamagnets 26, 26' could be measured and/or characterized during the "unexcited" periods. Decay in magnetization of the superparamagnet could also be measured.

To determine the positions of the superparamagnetic materials in three-dimensional space, four Hall effect sensors 28, 28', 28", 28"' could be carried by the cuff, as illustrated in FIGS. 24 and 25. Changes in the positions of the superparamagnetic materials 26, 26' in three-dimensional space could be used to determine changes in the joint space 25 or other positional changes in the implant components. Other types of magnetic sensors could be used instead of, or in addition to, the Hall effect sensors. Examples of such magnetic sensors include: variable reluctance sensors; magnetoelastic sensors; magnetoresistive sensors; magnetorestrictive sensors; saturation core (flux-gate) sensors; superconducting quantum interference devices (SQUIDS); nuclear magnetic resonance sensors; induction core magnetometers; proton precession magnetometers; and optically pumped magnetometers. All of these sensors are capable of sensing at least one property of an electromagnetic or magnetostatic field.

Instead of using an algorithm to calculate distances based on information from the Hall effect sensor(s) or transducer(s), the characteristics of the magnetic fields associated with a plurality of preselected distances could be determined empirically. Then, system could be based on these "signature" magnetic fields. In such a case, the data processor could be set up to store a number of signature magnetic fields for particular distances, and the characteristics of the magnetic fields sensed for a particular patient could be compared to these signature magnetic fields to determine the size of the joint space. Three-dimensional Hall effect sensors could be used in this mode of operation or in using an algorithm. It should be understood that other types of sensors that are capable of characterizing the magnetic field could be used; the invention is not limited to Hall effect sensors or to three-dimensional Hall effect sensors unless expressly called for in the claims.

In the embodiment of FIGS. 24–25, the Hall effect sensors or transducers 28, 28', 28", 28"' in the cuff 150 can be wired to the external data interpretation device 42, as shown schematically at 154. Alternatively a wireless communication can be used. The programming for converting the voltages produced by the Hall effect sensors or transducers into a usable distance or for characterizing the magnetic field(s) can be contained within the external data interpretation device 42. Moreover, in this embodiment, it is not necessary to utilize a transducer to convert the voltage to an RF signal for transmission to the external data interpretation device.

A hip endoprosthesis system 49 incorporating the principles of the present invention is illustrated in FIG. 7. In FIG. 7, the acetabular cup or shell is shown at 50 and the proximal femoral component is shown at 52. The proximal femoral component 52 has a femoral head 54 that bears against the surface of the acetabular liner 56, shown in phantom in FIG. 7. The articulation of this joint, shown at 58, is along the generally hemispherical inner surface of the acetabular liner 60. The thickness of the acetabular liner 56 corresponds with the joint space 62. In the embodiment of FIG. 7, the signal source 26 is affixed to the acetabular shell 50 and the sensor 28 is affixed to the proximal femoral component 52. Thus, as in the first illustrated embodiments, the signal source 26 and the sensor 28 are on opposite sides of the articulation 58 and on opposite sides of the joint space 62 or bearing 56. The electronics 30 are also affixed to the proximal femoral component 52 in the embodiment of FIG. 7. The electronics 30 may comprise the same elements as those described above for the embodiment of FIGS. 1–3. And like the embodiments described above, the signal source 26, sensor 28 and electronics 30 can be supplied assembled with the femoral and acetabular components 52, 54 or can be supplied as discrete elements to be affixed to the patient's bones. Use of the illustrated hip endoprosthesis system 49 would be similar to that described above for the knee endoprosthesis system.

Although the signal source 26 is shown associated with the acetabular cup in the case of the hip endoprosthesis, the invention is not limited to such an arrangement unless expressly called for in the claims. For example, the signal source 26 could be affixed to the proximal femoral component and the sensor 28 and electronics 30 could be affixed to the acetabular component 24 of the hip endoprosthesis system. Moreover, a system such as that shown in FIGS. 24–25 can be applied to a hip endoprosthesis system as well.

A shoulder endoprosthesis system 79 incorporating the principles of the present invention is illustrated in FIG. 12. In FIG. 12, the glenoid component is shown at 81 and the humeral component is shown at 83. The humeral component 83 has a humeral head 85 that bears against the articulating surface 87 of the glenoid component 81. The articulation of this joint, shown at 89, is along interface of the humeral head 85 and the articulating surface 87 of the glenoid component 81. The thickness of a portion of the glenoid component 81 corresponds with the joint space 91. In the embodiment of FIG. 12, the signal source 26 is affixed to the glenoid component 81 and the sensor 28 is affixed to the head 85 of the humeral component 83. Thus, as in the first illustrated embodiments, the signal source 26 and the sensor 28 are on opposite sides of the articulation 89 and on opposite sides of the joint space 91. The electronics 30 are affixed to the humeral component 83 in the embodiment of FIG. 12. The electronics 30 may comprise the same elements as those described above for the embodiment of FIGS. 1–3. And like the embodiments described above, the signal source 26, sensor 28 and electronics 30 can be supplied assembled with the humeral component 83 and glenoid component 81 or can be supplied as discrete elements to be affixed to the patient's bones. Use of the illustrated shoulder endoprosthesis system 79 would be similar to that described above for the knee endoprosthesis system.

Although the signal source 26 is shown associated with the glenoid component 81, the signal source 26 could be affixed to the humeral component 83 and the sensor 28 and electronics 30 could be affixed to the glenoid component 81 of the shoulder endoprosthesis system 79. Moreover, a system such as that shown in FIGS. 24–25 can be used for a shoulder endoprosthesis system as well.

An example of a knee endoprosthesis system using different types of signals is shown in FIG. 8. The same reference numbers have been used for the distal femoral 24, proximal tibial 18 and bearing 16 components of the system illustrated in FIG. 8 embodiment as those used for the embodiment of FIG. 1.

In the FIG. 8 embodiment, instead of the signal source 26 comprising a magnet, the signal source 26 comprises a radio-frequency (RF) transponder. This RF transponder is affixed on one side of the joint articulation 20 or joint space. In addition, instead of a Hall effect transducer, the sensor 28 comprises an RF receiver/demodulator that is affixed on the opposite side of the joint articulation 20 or joint space.

In addition to the RF receiver/demodulator serving as a sensor 28, the electronics 70 (see FIG. 9 schematic) affixed to or contained within the proximal tibial side of the illustrated knee endoprosthesis system include a power source 72, a digital logic element 74, a pulse generator 76, a printed circuit board 78, an internal transmitter 80, wiring 82 and solder (not shown). The power source 72 can be a ferrite coil functioning like that in the first illustrated embodiment, supplying power to the other electronics 70 when an external power source 84 such as an inductive coil is placed in proximity to exterior of the joint bearing the ferrite coil power source 72. A suitable digital logic element 74, pulse generator 76 and printed circuit board 78 would be electrically connected to the sensor 28, comprising the RF receiver/modulator in this embodiment, to generate a signal that can be transmitted to the internal transmitter 80 for transmission to an external receiver 86. The external receiver 86 is connected to an external data interpretation device 88 such as a computer, hand held personal data assistant, laptop or other programmable device for interpretation of the signal and conversion to a distance measurement.

Figure 9:
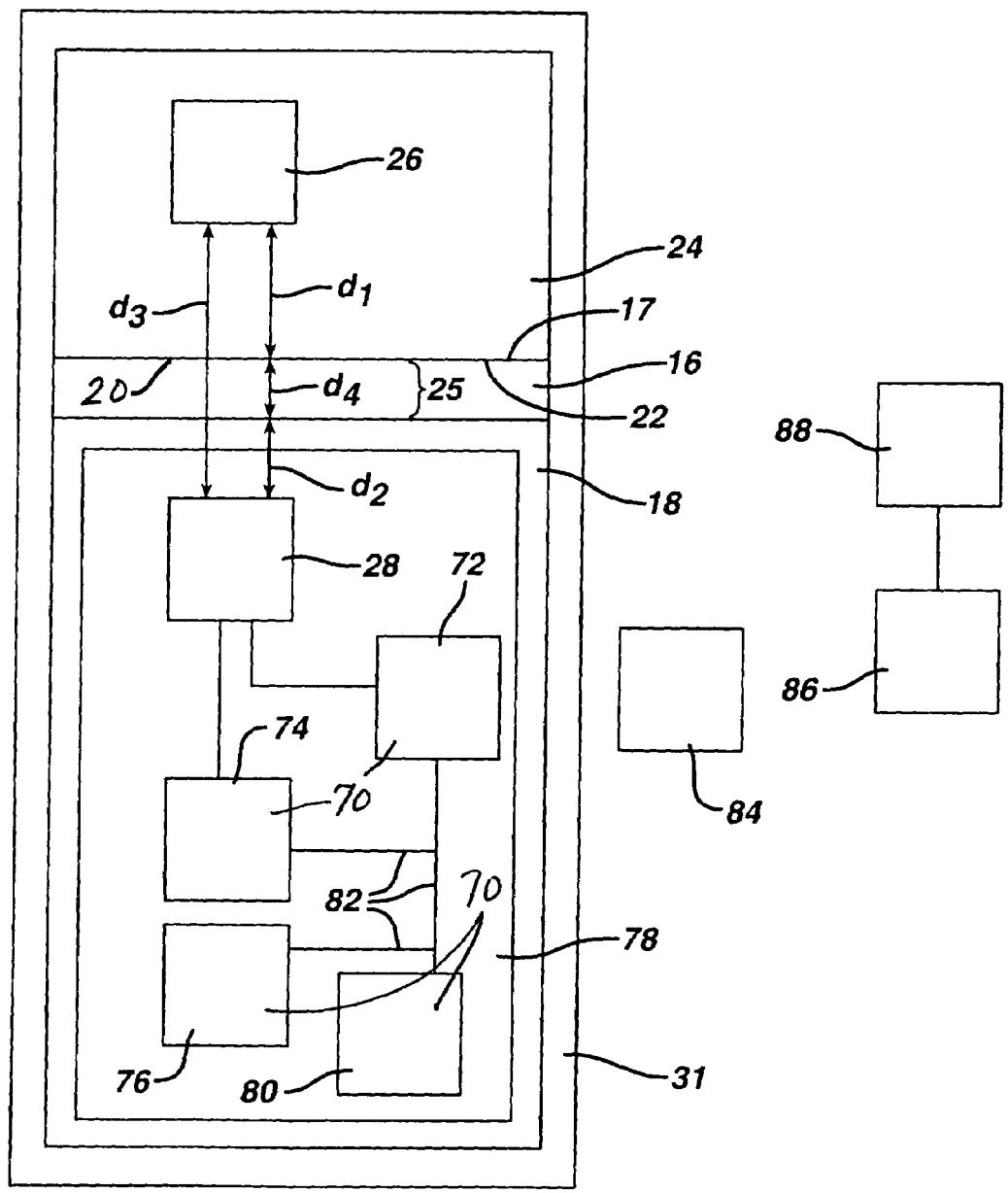
FIG. 9 is a schematic illustration of the knee endoprosthesis system of FIG. 8, showing external components of the system in addition to those implanted in the patient.

In the embodiment of FIGS. 8–9, the amplitude or phase of the signal received by the RF receiver/demodulator varies with the distance between the RF transponder serving as the signal source 26 and the RF receiver/demodulator serving as the sensor 28. Since a particular wave amplitude or phase corresponds with a specific distance between these elements, the amplitude or phase received by the sensor 28 (RF receiver/demodulator) can be converted to a distance that corresponds with the joint space or with a change in the joint space.

Thus, it should be understood that the signal characteristics that can be used in the various embodiments of the present invention include voltage, frequency, wave amplitude and phase, for example.

Figure 10:
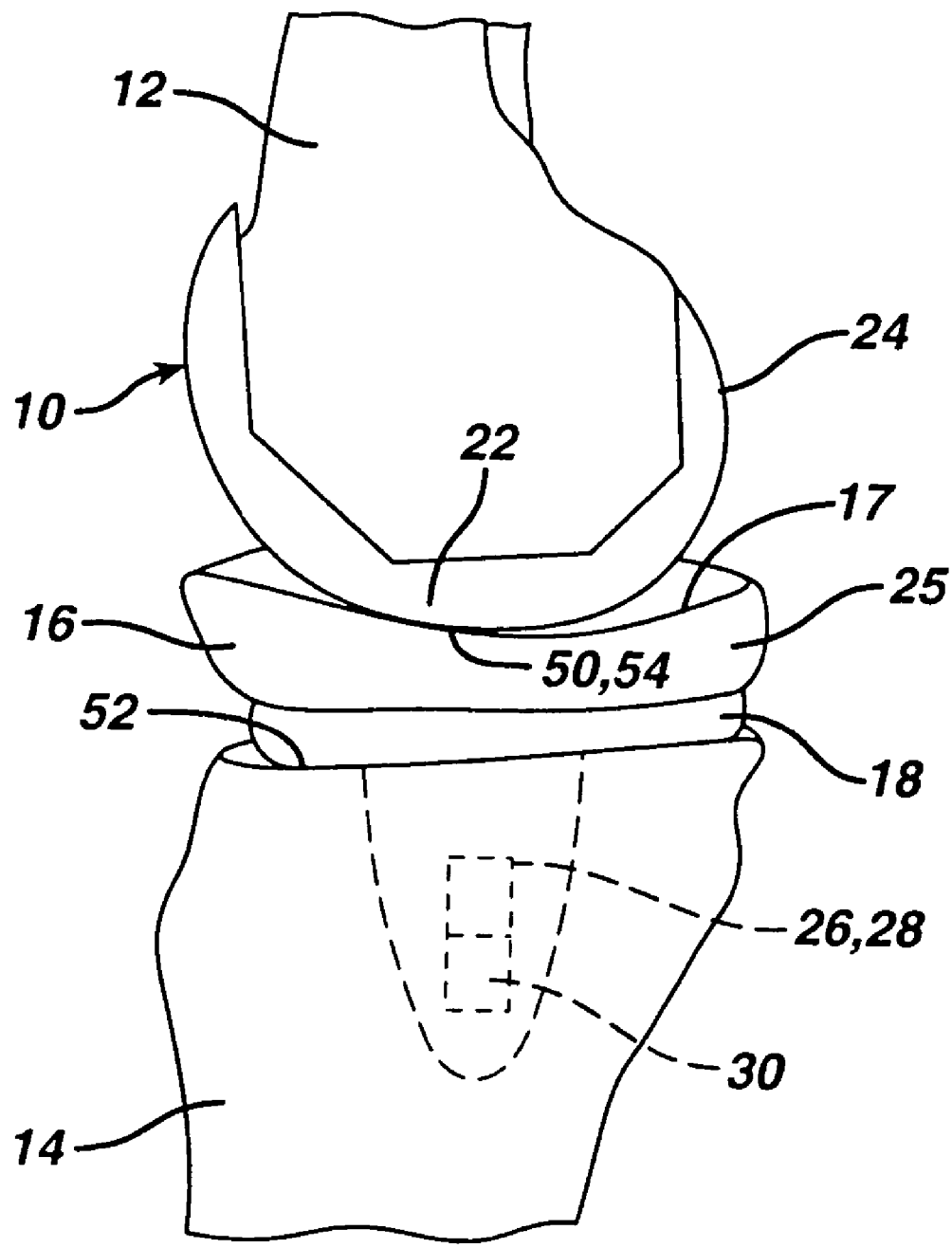
FIG. 10 is a medial/lateral elevation of another embodiment of a knee endoprosthesis system with the distal femoral component affixed to the distal femur and the proximal tibial component affixed to the proximal tibia, showing the knee joint in extension.
Figure 11:
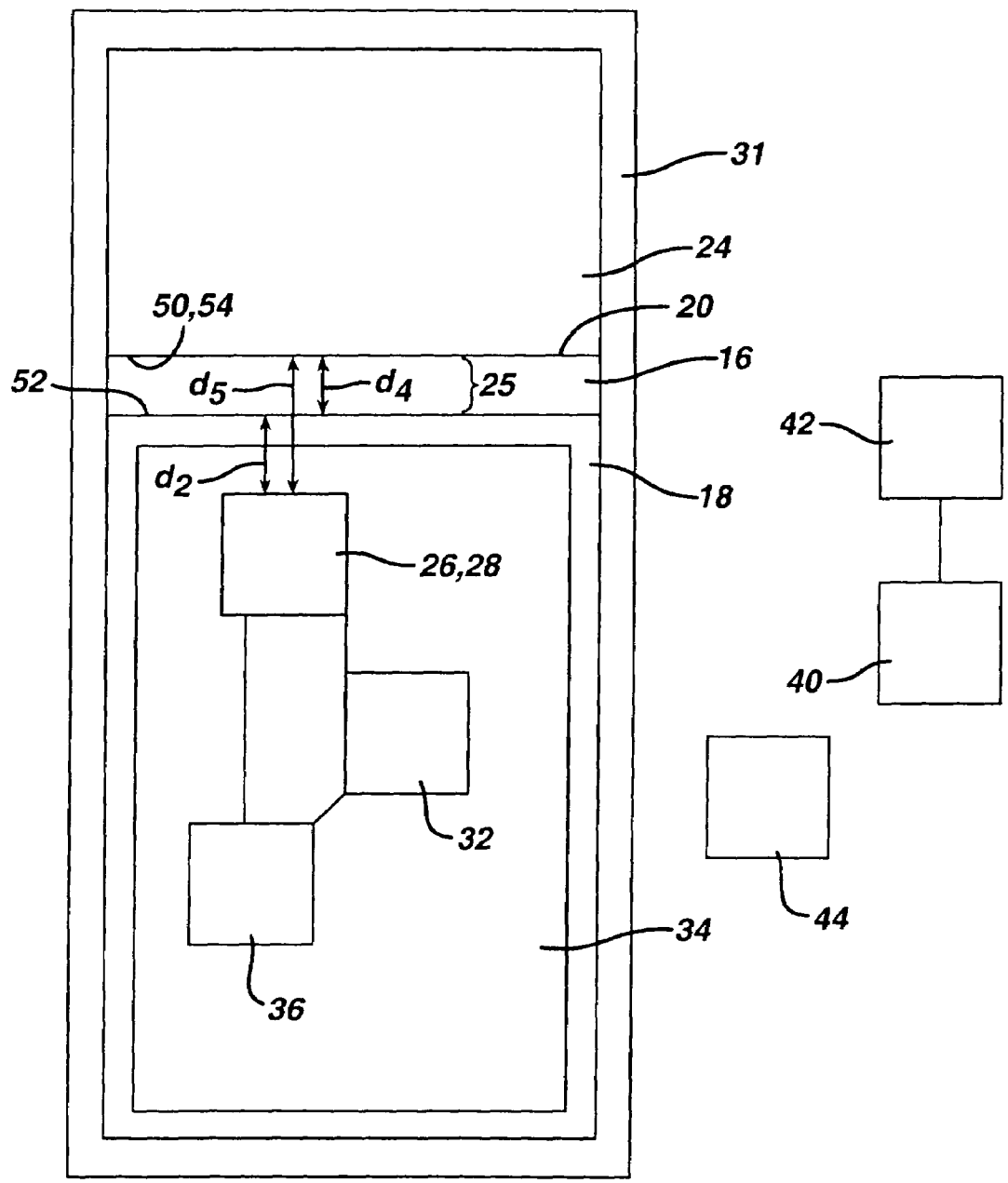
FIG. 11 is a schematic illustration of the knee endoprosthesis system of FIG. 10, showing external components of the system in addition to those implanted in the patient.

Another embodiment of a knee endoprosthesis system is illustrated in FIGS. 10–11. The same reference numbers have been used for the distal femoral 24, proximal tibial 18 and bearing 16 components of the systems illustrated in FIGS. 1 and 8 embodiments as those used for the embodiment of FIG. 10. In the embodiment of FIG. 10, the distance reference comprises a target 50 and the signal source 26 comprises an eddy current sensor.

The target 50 in the embodiment of FIG. 10 is a portion of the outer surface of the distal condylar portion of the distal femoral component 24. The eddy current sensor serves both as the signal source 26 and the sensor 28 in this embodiment, sensing eddy current loss at the target 50. The eddy current sensor in this embodiment is affixed to the tibial component 18, along with the remaining electronics 30. As shown in FIG. 11, the implanted electronics 30 may include an internal power source 32, a printed circuit board 34 and a transmitter 36 connected by wiring 38. An external power source 44, external receiver 40 and external computer 42 can be provided at the point of care. In this embodiment, the distance $d_2$ between the proximal surface 52 of the tibial component 18 is a known, fixed distance. The eddy current sensor 26, 28 measures the distance between the eddy current sensor 26, 28 and the distal condylar surface 54, shown at $d_5$ in FIG. 11. The difference between the distance $d_5$ and $d_2$ is the thickness of the joint space 25 and the thickness of the tibial bearing 16, shown at $d_4$ in FIG. 11.

Figure 13:
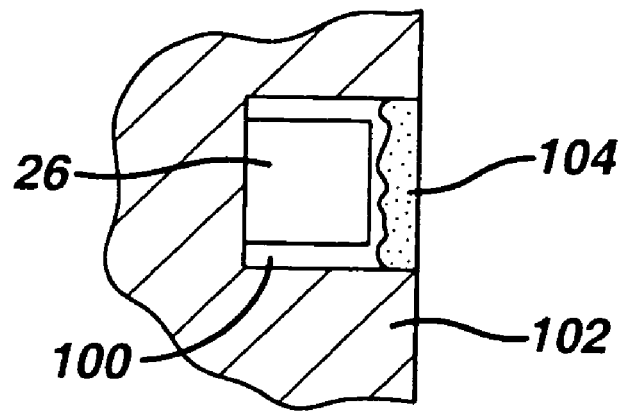
FIG. 13 is a partial cross-section of a portion of an endoprosthesis component with a signal source within a recess or cavity in the body portion of the endoprosthesis component.
Figure 14:
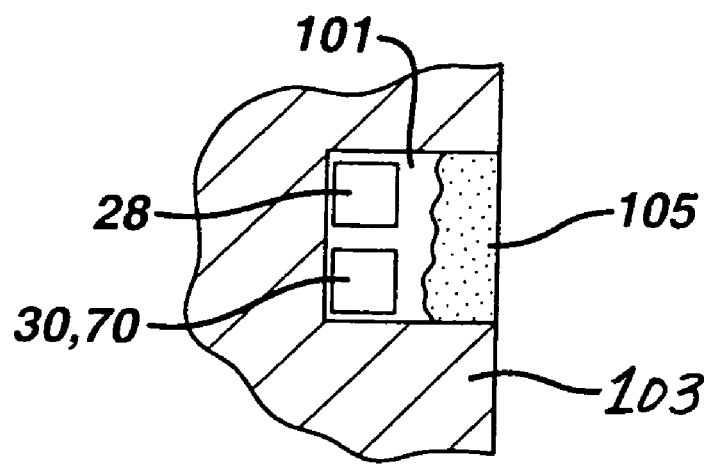
FIG. 14 is a partial cross-section of a portion of an endoprosthesis component with a sensor and electronics within a recess or cavity in the body portion of the endoprosthesis component.

In the embodiments illustrated in FIGS. 1, 4, 6–8, 10 and 12, the signal source 26, sensor 28 and associated electronics 30 could be held in recesses in the associated endoprosthesis components. FIGS. 13–14 illustrate recesses 100, 101 in the body 102, 103 of an endoprosthesis component. The body 102, 103 can be any of the components described above, such as the proximal tibial component 18, the tibial bearing 16, the distal femoral component 24, the proximal femoral component 52, the acetabular cup or shell 50, the acetabular liner 56, the humeral component 83, the glenoid component 81, or analogous components of other prosthetics. The recesses 100, 101 would be formed in areas of the endoprosthesis components where the presence of the recesses does not adversely affect the mechanical or physical properties of the endoprosthesis components. In the illustrated embodiments, the recesses or cavities 100, 101 extend inward from a non-articulating surface of the body 102, 103 of the endoprosthesis component. Similarly, the two signal sources 26, 26' of the embodiment of FIGS. 24–25 could be held in similar recesses in the implant components, and the signal source 26 of the embodiment of FIG. 15 could be held in a similar recess in the femoral component.

The sizes of the components 26, 26', 28, 30, 70 can be selected to minimize the amount of space required to be taken up by these components. Components can be combined if desired. The signal source 26, 26'. sensor 28, and associated electronics 30, 70 can be permanently affixed in these recesses with a suitable adhesive if desired. The recesses or cavities 100, 101 can be sealed by any appropriate means after the components are in place. For example, the openings to the recesses or cavities could be welded closed or a sealant such as a biocompatible epoxy or polyurethane could be poured over the recess or cavity as a liquid and allowed to cure, thereby permanently securing the components in the body of the prosthetic component. Cured sealant is indicated at 104, 105 in FIGS. 13–14.

It should be understood that while the signal source 26 could be within the interior of the prosthetic component or on or within bone rather than on an exposed surface of a prosthetic component, it may be possible or desirable to mount some of the electronics on a surface of one of the implants. Moreover, some of these electronic components could alternatively be formed as integral parts of the associated endoprosthesis components 16, 18, 24, 50, 52, 56, 81, 83.

It should be understood that other electronic components could be included in the kit or endoprosthesis system. For example, electronic components identifying the particular implant components could be included as part of each component.

In addition to using teachings of the present invention to measure a joint space or to determine changes in a joint space in two dimensions, the components of the joint endoprosthesis systems could provide signals giving one or more positions as a position in three-dimensional space. In such a case, a dimension or change in dimension could be measured as one or more vector dimensions between these points.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A joint endoprosthesis system for use in a joint comprising two bones interfacing at a joint articulation in a patient's body, the joint endoprosthesis system comprising:
a first prosthetic component;
a second prosthetic component;
a bearing component having a bearing surface to be placed against the first prosthetic component and a second surface to be placed against the second prosthetic component, the interface of the first prosthetic component and the bearing surface of the bearing component defining a joint articulation;
a signal source received within one of the prosthetic components on one side of the joint articulation and being capable of generating a first signal selected from the group consisting of a magnetic field and a magnetic flux density;
a sensor received within the other prosthetic component across the joint articulation from the signal source, the sensor being capable of producing a voltage, the magnitude of the voltage being dependent upon the magnitude of the first signal;
a modulator received within one of the prosthetic components and connected to receive the voltage generated by the sensor and being capable of converting the voltage received into a transmitter signal having a characteristic that varies depending on the magnitude of the voltage generated by the sensor; and
an internal transmitter received within one of the prosthetic components and connected to receive the transmitter signal from the modulator, the internal transmitter being capable of transmitting the transmitter signal from within the patient's body to a location outside of the patient's body.

2. The joint endoprosthesis system of claim 1 wherein the first prosthetic component comprises a distal femoral prosthesis having condyles and the second prosthetic component comprises a tibial prosthesis.

3. The joint endoprosthesis system of claim 1 wherein the first prosthetic component comprises an acetabular shell, the bearing comprises an acetabular liner and the second prosthetic component comprises a proximal femoral component having a femoral head with a surface for bearing against the acetabular liner.

4. The joint endoprosthesis system of claim 1 wherein the first prosthetic component comprises a humeral component and the second prosthetic component comprises a glenoid component.

5. The joint endoprosthesis system of claim 1 wherein: the sensor comprises a Hall effect transducer; the signal source comprises a permanent magnet and the modulator converts the voltage received from the Hall effect transducer into a radio-frequency wave.

6. The joint endoprosthesis system of claim 1 including an antenna received within one of the prosthetic components and coupled to the internal transmitter for transmitting the transmitter signal to a position outside of the patient's body.

7. The joint endoprosthesis system of claim 1 wherein the first signal includes a magnetic field.

8. The joint endoprosthesis system of claim 1 further comprising a power source to be implanted in the patient's body.

9. The joint endoprosthesis system of claim 5 wherein the first prosthetic component comprises a distal femoral component and the second prosthetic component comprises a tibial prosthesis.

10. The joint endoprosthesis system of claim 5 wherein the first prosthetic component comprises a femoral head, the second prosthetic component comprises an acetabular shell, and the bearing comprises an acetabular liner.

11. The joint endoprosthesis system of claim 5 wherein the first prosthetic component comprises a humeral component and the second prosthetic component comprises a glenoid component.

12. The joint endoprosthesis system of claim 1 wherein the modulator and transmitter comprise a single electronic element.

13. The joint endoprosthesis system of claim 1 wherein the modulator and transmitter comprise discrete electronic elements.

14. The joint endoprosthesis of claim 8 wherein the power source comprises a ferrite coil.

15. The joint endoprosthesis of claim 8 wherein the power source comprises a battery.

16. A method of determining a dimension of a joint space in the body of a patient wherein the patient has a joint endoprosthesis that includes a first prosthetic component and a bearing occupying the joint space adjacent the first prosthetic component, the method comprising: generating a voltage within the patient's body that has a characteristic that relates to a dimension of the joint space; modulating the voltage within the patient's body to produce a transmitter signal; transmitting the transmitter signal from within the patient's body to a location outside of the patient's body, wherein the transmitted signal has a characteristic that relates to the characteristic of the voltage; determining a dimension of the joint space based on the value of the characteristic of the transmitter signal.

17. The method of claim 16 wherein the step of generating a voltage comprises generating a magnetic field across the joint space.

18. The method of claim 17 wherein the magnetic field is generated on one side of the joint space and wherein the step of generating a voltage includes sensing a property of the magnetic field on the opposite side of the joint space.

19. The method of claim 18 wherein the step of modulating the voltage to produce a transmitter signal comprises producing a radio-frequency wave.

20. The method of claim 16 wherein the joint comprises the knee, the first prosthetic component comprises a distal femoral component and the bearing comprises a tibial bearing occupying a joint space adjacent the distal femoral component.

21. The method of claim 16 wherein the joint comprises the hip, the first prosthetic component comprises a proximal femoral component and the bearing comprises an acetabular liner.

22. The method of claim 16 wherein the joint comprises the shoulder, the first prosthetic component comprises a humeral component and the bearing comprises a glenoid component.

23. A method of determining a change in a dimension of a joint space in the body of a patient wherein the patient has a joint endoprosthesis that includes a first prosthetic component and a bearing occupying the joint space adjacent the first prosthetic component, the method comprising: generating a first signal from one side of the joint space at a first location within the patient's body; receiving the first signal on the opposite side of the joint space at a second location within the patient's body; producing a voltage within the patient's body, where the magnitude of the voltage depends upon a characteristic of the first signal; modulating the voltage within the patient's body to produce a transmitter signal a characteristic of which depends upon the magnitude of the voltage produced; transmitting the transmitter signal from within the patient's body to an external location; determining the extent of change in a dimension of the joint space based on said characteristic of the transmitter signal.

24. The method of claim 23 wherein the step of generating a first signal creates a magnetic field at the second location.

25. The method of claim 23 wherein the step of modulating the voltage includes generating a radio-frequency wave.

26. The method of claim 25 wherein the characteristic of the radio-frequency wave that relates to distance between the first location and the second location includes at least one of the following: frequency, amplitude and phase.

27. The method of claim 23 wherein the joint comprises the knee, the first prosthetic component comprises a distal femoral component and the bearing comprises a tibial bearing occupying a joint space adjacent the distal femoral component.

28. The method of claim 23 wherein the joint comprises the hip, the first prosthetic component comprises a proximal femoral component and the bearing comprises an acetabular liner.

29. The method of claim 23 wherein the joint comprises the shoulder, the first prosthetic component comprises a humeral component and the bearing comprises a glenoid component.

30. A joint endoprosthesis system for use in a joint comprising two bones interfacing at a joint articulation in a patient's body, the joint endoprosthesis system comprising: a first prosthetic component; a second prosthetic component; a bearing having a bearing surface to be placed against the first prosthetic component and a second surface facing the second prosthetic component, the interface of the first prosthetic component and the bearing surface of the bearing defining a joint articulation; a magnet affixed within one of the prosthetic components; a sensor affixed within the other prosthetic component, the sensor being capable of sensing a property of the magnetic field of the magnet and producing a voltage the magnitude of which depends upon the sensed property of the magnetic field; and a modulator received within one of the prosthetic components and connected to receive the voltage produced by the sensor, the modulator being capable of producing a signal having a characteristic that varies depending on the voltage received from the sensor and that is capable of being transmitted from within the patient's body to a location outside of the patient's body.

31. The joint endoprosthesis system of claim 30 wherein the sensor is selected from the group consisting of: a Hall effect sensor; a three-dimensional Hall effect sensor; a variable reluctance sensor; a magnetoelastic sensor; a magnetoresistive sensor; a magnetorestrictive sensor; a saturation core sensor; a superconducting quantum interference device; a nuclear magnetic resonance sensor; am induction core magnetometer; a proton precession magnetometer; and an optically pumped magnetometer.

32. The joint endoprosthesis of claim 30 further comprising a power source to be implanted in the patient's body.

33. The joint endoprosthesis system of claim 30 wherein the magnet is carried by one of the prosthetic components and the sensor is carried by the other prosthetic component.

34. The joint endoprosthesis of claim 32 wherein the power source comprises a ferrite coil.

35. The joint endoprosthesis of claim 32 wherein the power source comprises a battery.

36. The joint endoprosthesis of claim 34 wherein the magnets comprise superparamagnets and the cuff includes a magnetic field source.

37. A joint endoprosthesis system for use in a joint comprising two bones interfacing at a joint articulation in a patient's body, the joint endoprosthesis system comprising: a first prosthetic component; a second prosthetic component; a bearing having a bearing surface to be placed against the first prosthetic component and an opposite surface to face the second prosthetic component, the interface of the first prosthetic component and the bearing surface of the bearing defining a joint articulation; a magnet affixed to one of the prosthetic components; and an external cuff separate from the first prosthetic component, second prosthetic component and bearing, the external cuff including a sensor to be maintained outside of the patient's body, the sensor being capable of sensing a property of the magnetic field of the magnet.

38. The joint endoprosthesis system of claim 37 wherein the sensor is selected from the group consisting of: a Hall effect sensor; a three-dimensional Hall effect sensor; a variable reluctance sensor; a magnetoelastic sensor; a magnetoresistive sensor; a magnetorestrictive sensor; a saturation core sensor; a superconducting quantum interference device; a nuclear magnetic resonance sensor; an induction core magnetometer; a proton precession magnetometer; and an optically pumped magnetometer.

39. The joint endoprosthesis system of claim 37 wherein the external cuff is inflatable.

40. The joint endoprosthesis system of claim 37 wherein the cuff includes an additional sensor.

41. The joint endoprosthesis system of claim 37 wherein the cuff includes an additional plurality of sensors.

42. The joint endoprosthesis of claim 37 further comprising an additional magnet affixed to one of the prosthetic components.

43. The joint endoprosthesis of claim 41 wherein the sensors are selected from the group consisting of: a Hall effect sensor; a three-dimensional Hall effect sensor; a variable reluctance sensor; a magnetoelastic sensor; a magnetoresistive sensor; a magnetorestrictive sensor; a saturation core sensor; a superconducting quantum interference device; a nuclear magnetic resonance sensor; an induction core magnetometer; a proton precession magnetometer; and an optically pumped magnetometer.

* * * * *